United States Patent
Newberry et al.

(10) Patent No.: US 9,636,457 B2
(45) Date of Patent: May 2, 2017

(54) SYSTEM AND METHOD FOR A DRUG DELIVERY AND BIOSENSOR PATCH

(71) Applicant: Sanmina Corporation, San Jose, CA (US)

(72) Inventors: Robert Steven Newberry, New Hope, AL (US); Matthew Rodencal, Huntsville, AL (US)

(73) Assignee: SANMINA CORPORATION, San Jose, CA (US)

( * ) Notice: Subject to any disclaimer, the term of this patent is extended or adjusted under 35 U.S.C. 154(b) by 0 days.

(21) Appl. No.: 15/276,760

(22) Filed: Sep. 26, 2016

(65) Prior Publication Data

US 2017/0014572 A1 Jan. 19, 2017

Related U.S. Application Data

(63) Continuation-in-part of application No. 14/866,500, filed on Sep. 25, 2015, and a continuation-in-part of
(Continued)

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14248* (2013.01); *A61M 5/3298* (2013.01);
(Continued)

(58) Field of Classification Search
CPC .... A61M 5/1723; A61M 5/158; A61M 5/145; A61M 5/14248; A61M 2205/3306;
(Continued)

(56) References Cited

U.S. PATENT DOCUMENTS 5,269,310 A 12/1993 Jones et al.
5,515,847 A * 5/1996 Braig ................ A61B 5/14532
600/316
(Continued)

OTHER PUBLICATIONS

KC Manhesh et al., Wearable Wireless Intelligent Multi-Parameter Health Monitoring Watch, 2013, Texas Instruments India Educators' Conference, IEEE, p. 61-64.
(Continued)

*Primary Examiner* — Manuel Mendez
(74) *Attorney, Agent, or Firm* — Loza & Loza, LLP; Julio Loza

(57) ABSTRACT

An integrated drug delivery and biosensor (IDDB) system is implemented on a patch or arm band. The drug delivery system includes needles adapted to pierce the skin and direct injection of a predetermined dosage of medication through the needles into the epidermis of the skin of a patient. The integrated biosensor monitors absorption of the medication into the epidermis of the skin of the patient and may also monitor concentration of the medication or other relevant substances in arterial blood flow of the patient. The integrated biosensor may also monitor a patient's vitals in response to the medication. The integrated biosensor may then alter dosage or frequency of administration of dosages or even halt a dosage of medication in response to the patient's vitals or absorption of the medication.

23 Claims, 18 Drawing Sheets

Related U.S. Application Data application No. 15/275,388, filed on Sep. 24, 2016, and a continuation-in-part of application No. 15/275,444, filed on Sep. 25, 2016.

(60) Provisional application No. 62/194,264, filed on Jul. 19, 2015, provisional application No. 62/276,934, filed on Jan. 10, 2016, provisional application No. 62/307,375, filed on Mar. 11, 2016, provisional application No. 62/312,614, filed on Mar. 24, 2016, provisional application No. 62/373,283, filed on Aug. 10, 2016, provisional application No. 62/383,313, filed on Sep. 2, 2016.

(51) Int. Cl.
*A61M 5/32* (2006.01)
*A61M 5/145* (2006.01)

(52) U.S. Cl.
CPC ..... *A61M 5/145* (2013.01); *A61M 2205/3306* (2013.01); *A61M 2205/3584* (2013.01); *A61M 2205/502* (2013.01); *A61M 2205/52* (2013.01); *A61M 2205/8206* (2013.01); *A61M 2205/8268* (2013.01); *A61M 2230/06* (2013.01); *A61M 2230/20* (2013.01); *A61M 2230/30* (2013.01); *A61M 2230/42* (2013.01); *A61M 2230/50* (2013.01); *A61M 2230/63* (2013.01)

(58) Field of Classification Search
CPC .......... A61M 2230/42; A61M 2230/06; A61M 2230/63; A61M 2205/502; A61M 2230/20; A61M 2230/30; A61M 2205/8268; A61M 2205/8206; A61M 2205/52; A61M 2230/50; A61M 2205/3584
USPC ....... 604/65–67, 131, 151; 128/DIG. 12, 13; 600/558, 316
See application file for complete search history.

(56) References Cited

U.S. PATENT DOCUMENTS

| | | |
|---|---|---|
| 6,985,763 B2 | 1/2006 | Boas et al. |
| 9,149,216 B2 | 10/2015 | Eisen et al. |
| 2002/0049389 A1* | 4/2002 | Abreu ................. A61B 3/1241 600/558 |
| 2008/0208019 A1 | 8/2008 | Nitzan |
| 2008/0241199 A1 | 10/2008 | Silverman |
| 2009/0156988 A1 | 6/2009 | Ferren et al. |
| 2009/0187167 A1 | 7/2009 | Sexton et al. |
| 2011/0106050 A1* | 5/2011 | Yodfat ............. A61M 5/14248 604/504 |
| 2011/0160697 A1* | 6/2011 | Yodfat ................... A61B 18/14 604/506 |
| 2011/0166553 A1 | 7/2011 | Holmes et al. |
| 2013/0110311 A1 | 5/2013 | Steeg et al. |
| 2013/0310669 A1 | 11/2013 | Nitzan |
| 2014/0112940 A1 | 4/2014 | Lane |
| 2015/0094914 A1 | 4/2015 | Abreu |
| 2015/0109617 A1 | 4/2015 | Gilbert et al. |
| 2015/0150453 A1 | 6/2015 | Abreu |
| 2015/0182172 A1 | 7/2015 | Shelley et al. |
| 2015/0282747 A1 | 10/2015 | Thiele |
| 2015/0366471 A1 | 12/2015 | LeBoeuf et al. |
| 2016/0018257 A1 | 1/2016 | Mirov et al. |
| 2016/0058347 A1 | 3/2016 | Reichgott et al. |
| 2016/0066863 A1 | 3/2016 | Thaveeprungsriporn et al. |
| 2016/0100781 A1 | 4/2016 | Bechtel et al. |

OTHER PUBLICATIONS

Abdallah et al., Design of a Compact Multi-Sensor System for Non-Invasive Glucose Monitoring Using Optical Spectroscopy, International Conference on Electronics, Biomedical Engineering and its Applications (ICEBEA'2012), Jan. 7-8, 2012, p. 310-317.

Forst et al., Cardiovascular Effects of Disturbed Insulin Activity in Metabolic Syndrome and in Type 2 Diabetic Patients, Insulin Secretion and Action, Horm Metab Res; 2009, 41; p. 123-131.

Mohamed Elgendi, On the Analysis of Fingertip Photoplethysmogram Signals, Current Cardiology Reviews, 2012, 8, p. 14-25, Bentham Science Publishers.

Wikipedia, Cytochrome P450, Dec. 31, 2015, p. 1-12.

Oliver Wieben, Light Absorbance in Pulse Oximetry, Taylor & Francis, 1997, IOP Publishing, p. 1-20.

Wikipedia, Photoplethysmogram, Jul. 25, 2015, p. 1-4.

PCT/US2016/053845. Int'l Search Report & Written Opinion (Dec. 28, 2016).

* cited by examiner

SYSTEM AND METHOD FOR A DRUG DELIVERY AND BIOSENSOR PATCH

CLAIM OF PRIORITY UNDER 35 U.S.C. §119 AND §120

The present application claims priority under 35 U.S.C. §120 as a continuation in part application to U.S. Utility application Ser. No. 14/866,500 entitled, "System and Method for Glucose Monitoring," filed Sep. 25, 2015, which claims priority under 35 U.S.C. §119 to U.S. Provisional Application No. 62/194,264 entitled, "System and Method for Glucose Monitoring," filed Jul. 19, 2015, both of which are hereby expressly incorporated by reference herein. The present application claims priority under 35 U.S.C. §119 to U.S. Provisional Application No. 62/276,934 entitled, "System and Method for Health Monitoring including a Remote Device," filed Jan. 10, 2016, and hereby expressly incorporated by reference herein. The present application claims priority under 35 U.S.C. §119 to U.S. Provisional Application No. 62/307,375 entitled, "System and Method for Health Monitoring using a Non-Invasive, Multi-Band Sensor," filed Mar. 11, 2016, and hereby expressly incorporated by reference herein. The present application claims priority under 35 U.S.C. §119 to U.S. Provisional Application No. 62/312,614 entitled, "System and Method for Determining Biosensor Data using a Broad Spectrum Light Source," filed Mar. 24, 2016, and hereby expressly incorporated by reference herein. The present application claims priority under 35 U.S.C. §119 to U.S. Provisional Application No. 62/373,283 entitled, "System and Method for a Biosensor Monitoring and Tracking Band," filed Aug. 10, 2016, and hereby expressly incorporated by reference herein. The present application claims priority under 35 U.S.C. §119 to U.S. Provisional Application No. 62/383,313 entitled, "System and Method for a Drug Delivery and Biosensor Patch," filed Sep. 2, 2016, and hereby expressly incorporated by reference herein. The present application claims priority as a continuation in part under 35 U.S.C. §120 to U.S. Utility application Ser. No. 15/275,388 entitled, "System And Method For Health Monitoring Using A Non-Invasive, Multi-Band Biosensor," filed Sep. 24, 2016, and hereby expressly incorporated by reference herein. The present application claims priority as a continuation in part under 35 U.S.C. §120 to U.S. application Ser. No. 15/275,444, entitled, "System And Method For A Biosensor Monitoring And Tracking Band" filed on September 25, and hereby expressly incorporated by reference herein.

FIELD

This application relates to a systems and methods of non-invasive, autonomous health monitoring and drug delivery system, and in particular a health monitoring and drug delivery patch that assists in tracking a patient's vitals and delivering a medication to the patient using needles.

BACKGROUND

A patient's vitals, such as temperature, blood oxygen levels, blood pressure, etc., may need to be monitored periodically typically using one or more instruments. For example, instruments for obtaining vitals of a patient include blood pressure cuffs, thermometers, $SO_2$ measurement devices, glucose level meters, etc. Often, multiple instruments must be brought to a patient's room by a caretaker, and the measurements collected using the multiple instruments. This monitoring process can be time consuming, inconvenient and is not always continuous. It may also disrupt sleep of the patient. The measurements of the vitals must then be manually recorded into the patient's electronic medical record.

In addition, one or more medications may need to be administered to a patient. Medications may be administered, e.g. intravenously or orally. The dosage of the medications is predetermined prior to administration orally or prior to applying the medication to an intravenous system. There currently is no continuous or real-time measurement of efficacy or absorption rates of the dosage of medication.

As such, there is a need for a patient monitoring system that includes an accurate, continuous and non-invasive biosensor that may measure patient vitals, and deliver medication in response to the patient's vitals.

SUMMARY

According to a first aspect, an integrated drug delivery and biosensor (IDDB) system is implemented on a patch configured for attaching to a patient. The IDDB system includes a drug delivery system coupled to the patch, wherein the drug delivery system is configured to administer a dosage of medication at an administration rate to the patient. The IDDB system also includes a biosensor system coupled to the patch, wherein the biosensor system is configured to monitor biosensor data of the patient, wherein the biosensor data includes one or more of: respiratory rate, heart rate or blood pressure; monitor absorption rate of the medication into one or more of: surrounding tissue or arterial blood flow; and monitor concentration of a substance in one or more of: surrounding tissue or arterial blood flow. The drug delivery system is further configured to alter at least one of the dosage of the medication or the administration rate of the medication in response to the biosensor data.

According to a second aspect, an integrated drug delivery and biosensor (IDDB) system is implemented on a patch configured for attaching to a patient. The IDDB system includes a drug delivery system coupled to the patch, wherein the drug delivery system is configured to administer medication to the patient. The IDDB system also includes a biosensor coupled to the patch, wherein the biosensor system is configured to monitor biosensor data of the patient, wherein the biosensor data includes one or more of: respiratory rate, heart rate or blood pressure and monitor concentration of a substance in one or more of: surrounding tissue or arterial blood flow. The IDDB system is further configured to determine when one or more predetermined thresholds are detected in the biosensor data of the patient or the concentration of the substance; and transmit instructions to the drug delivery system to administer a dosage of the medication in response to the biosensor data.

According to a third aspect, an integrated drug delivery and biosensor (IDDB) system is implemented on a patch configured for attaching to a patient and includes a drug delivery system and a biosensor. The drug delivery system is configured to administer medication to the patient and the biosensor includes a light source configured to emit light directed at skin of the patient at a plurality of frequencies; a photodetector circuit configured to detect spectral responses of reflected light from the skin and surrounding tissue at the plurality of frequencies; and a processing circuit. The processing circuit is configured to: process the spectral responses at the plurality of frequencies; obtain a concentration level of at least one substance in arterial blood flow of the patient using the spectral responses at the plurality of frequencies; and determine an absorption rate of the medication in surrounding tissue of the patient using the spectral responses at the plurality of frequencies. The processing circuit is further configured to determine when one or more predetermined thresholds are detected in the biosensor data of the patient or the concentration of the substance; and transmit instructions to the drug delivery system to administer a dosage of the medication in response to the biosensor data.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview—Integrated Drug Delivery and Biosensor System

An integrated drug delivery and biosensor (IDDB) system is implemented on a compact form factor such as on a patch or arm band. The drug delivery system includes one or more needles adapted to pierce the skin and a drug receptacle. A hydrogen fuel cell is configured to pressurize the drug receptacle and force a predetermined dosage of medication through the needles into the epidermis of the skin of a patient. The integrated biosensor monitors absorption of the medication into the epidermis of the skin of the patient and may also monitor concentration of the medication in arterial blood flow of the patient. The integrated biosensor may also monitor a patient's vitals in response to the medication. The integrated biosensor may then alter dosage or frequency of administration of dosages or even halt a dosage of medication in response to the patient's vitals or absorption of the medication.

Embodiment—IDDB System

Figure 1A:
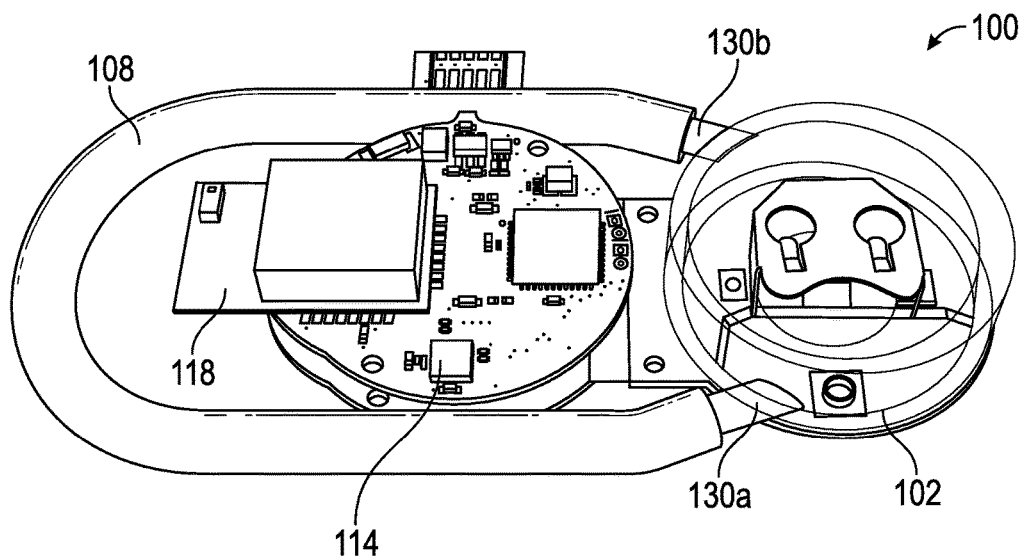
FIG. 1A and FIG. 1B illustrate perspective views of an exemplary embodiment of the integrated drug delivery and biosensor (IDDB) system.
Figure 1B:
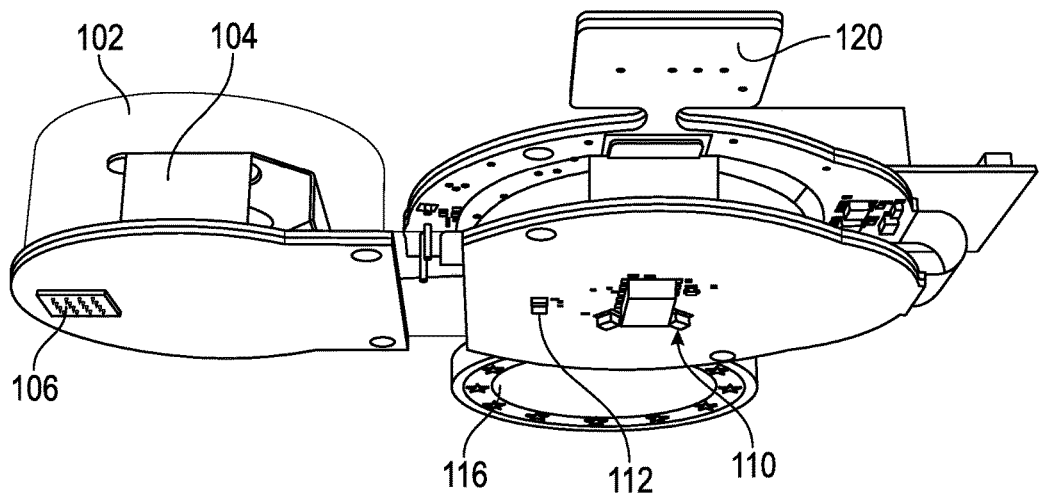

FIG. 1A and FIG. 1B illustrate perspective views of an exemplary embodiment of the integrated drug delivery and biosensor (IDDB) system 100. The IDDB system 100 may be implemented on a wearable patch that includes a drug delivery system and a biosensor. The drug delivery system includes a drug receptacle 102 with an embedded fuel cell 104, one or more needles 106, and tubing 108 connecting the drug receptacle to the one or more needles 106. The needles 106 are configured to pierce at least the upper epidermis of skin of a patient (human or animal) to administer medication to the patient.

In one aspect, the fuel cell 104 releases a predetermined amount of fuel, such as hydrogen, to pressurize the tubing 108 and force a dosage of medication from the drug receptacle 102 through the needles 106 into the skin. The pressure asserted by the fuel cell 104 may vary to control the dosage of medication and time release of the medication. For example, the dosage of the medication may be administered at various rates, e.g. slowly over several minutes, hours or days, or relatively quickly over microseconds, by varying the pressure asserted by the fuel.

In another aspect, the needles 106 or a coating over the needles 106 may be electrochemically doped with medication. The needles 106 are then stimulated with an electric current to release the medication. The applied electrical current may be varied to control the dosage of medication and time release of the medication.

The biosensor further includes one or more sensors for detecting biosensor data, such as a patient vitals, activity levels, and concentrations of substances in the patient. For example, the biosensor system may include a temperature sensor 112 having an array of sensors (e.g., 16×16 pixels) positioned facing or adjacent to the skin of the patient to measure temperature. The biosensor system may also include a photoplethysmograpy (PPG) circuit 110. The PPG circuit 110 may be configured to detect $SPO_2$ levels, heart rate, blood pressure and/or concentration of substances in arterial blood flow of the patient as described in more detail herein. The biosensor may also include an activity monitoring circuit 114 configured to determine an activity level or positioning of a patient. For example, the activity monitoring circuit 114 may include a multiple axes six degrees of freedom (6 DOF) inertial motion capture system with initial orientation determination capability.

In another aspect, one or more optical fibers may be inserted within the needles 106 and optically coupled to the PPG circuit 110. The PPG circuit 110 transmits and detects light through the optical fibers to monitor absorption of the medication into the skin and surrounding tissue of the patient using Beer-Lambert principles described in more detail herein. For example, the PPG circuit 110 is configured to transmit light at one or more wavelengths through the optical fibers onto the skin of the patient and detect the reflected light spectrum at the one or more wavelengths. The PPG circuit 110 using spectroscopy or PPG techniques described in further detail herein may then determine a concentration of the medication in the epidermis of the skin and surrounding tissue. The PPG circuit 110 may monitor the concentration of the medication over a time period to determine an absorption rate of the medication into the skin and surrounding tissue of the patient. The PPG circuit 110 may also monitor concentration of the medication or other substances in the surrounding tissue or arterial blood flow to determine efficacy of the medication. The IDDB system 100 may then determine a personal profile for the patient of the absorption rate, concentration levels of relevant substances in the arterial blood stream and patient vitals over time during and after a dosage of medication. These profiles may also be correlated with the measured activity level of the patient or other patient biosensor data.

The IDDB system 100 is configured to continuously monitor biosensor data, such as absorption of the medication, patient vitals and/or concentration of the medication or other relevant substances in the surrounding tissue and in the arterial blood flow while the medication is administered and thereafter. In response thereto, the IDDB system 100 may then determine to halt administration of a dosage of the medication, e.g. when an allergic reaction is detected through patient vitals. The IDDB system 100 may also determine to alter a dosage amount or frequency of administration of a dosage or rate of administration of a dosage of the medication in response to the biosensor data.

In another aspect, the IDDB system 100 monitors patient vitals and/or concentration of relevant substances in the arterial blood flow of the patient and then determines to administer medication in response thereto. For example, the IDDB system 100 may detect a predetermined threshold of glucose levels or insulin response in arterial blood flow and determine to administer a dosage of insulin in response thereto. In another example, the biosensor system may determine an allergic reaction in a patient based on biosensor data and determine to administer epinephrine in response thereto. The dosage amount and the frequency and rate of administration of the medication may be adjusted in response to biosensor feedback as well.

The IDDB system 100 further includes a battery 116 and a wireless transceiver 118 configured to communicate instructions and biosensor data to and from the IDDB system 100. The IDDB system 100 may also include a joint test action group (JTAG) header 120 for programming and testing of the IDDB system 100 at manufacture.

Figure 2:
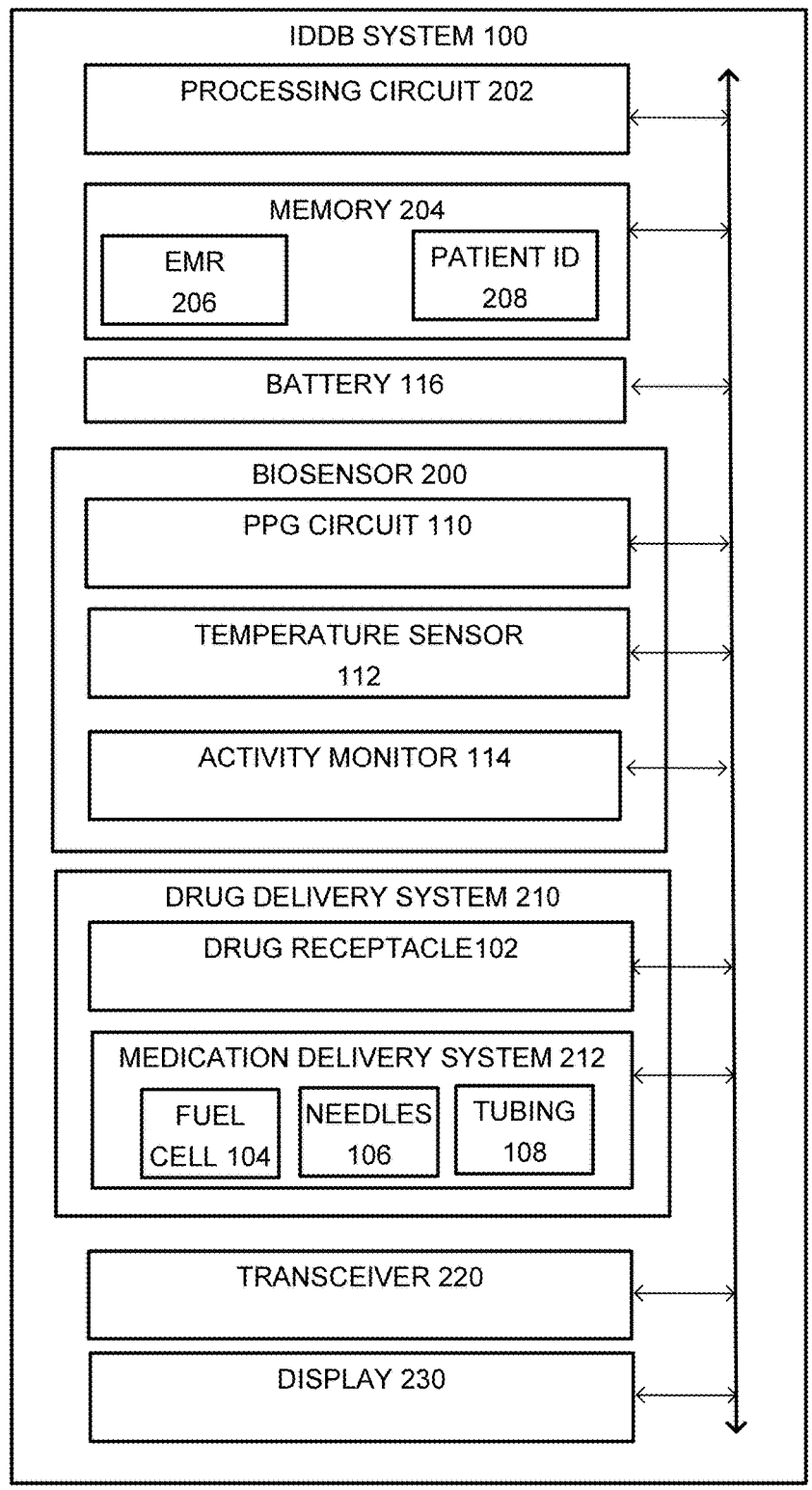
FIG. 2 illustrates a schematic block diagram of an embodiment of the IDDB system

FIG. 2 illustrates a schematic block diagram of an embodiment of the IDDB system 100. The IDDB system 100 includes one or more processing circuits 202 communicatively coupled to a memory device 204. In one aspect, the memory device 204 may include one or more non-transitory processor readable memories that store instructions which when executed by the processing circuit 202, causes the processing circuit 202 to perform one or more functions described herein. The memory device 204 may also include an EEPROM or other type of memory to store a patient identification (ID) 208 that is associated with a patient being monitored by the biosensor 200. The memory device 104 may also store an electronic medical record (EMR) 206 or portion of the EMR associated with the patient being monitored by the biosensor 200. The biosensor data obtained by the biosensor 200 may be stored in the EMR as well as the patient medical history. The processing circuit 202 may be co-located with one or more of the other circuits of the IDDB system 100 in a same physical encasement or located separately in a different physical encasement or located remotely. In an embodiment, IDDB system 100 is battery operated and includes a battery 116, such as a lithium ion battery. IDDB system 100 may also include a display configured to display 230.

The IDDB system 100 further includes a transceiver 220. The transceiver 220 may include one or more types of wireless or wired transceivers. For example, the transceiver 220 may be configured to communicate with one or more devices over a LAN, MAN and/or WAN. In one aspect, the wireless transceiver may include IEEE 802.11ah, Zigbee, IEEE 802.15-11 or WLAN (such as an IEEE 802.11 standard protocol) compliant transceiver. In another aspect, the wireless transceiver may also include or alternatively include an interface for communicating over a cellular network. The transceiver may also include a near field transceiver that may operate using RFID, short range radio frequency, Bluetooth, infrared link, or other short range wireless communication protocol. The near field transceiver may transmit the patient identification (ID) 208 and biosensor data over a short range to local devices. In an embodiment, the wireless transceiver may include a thin foil for an antenna that is specially cut and includes a carbon pad contact to a main PCB of the IDDB system 100. This type of antenna is inexpensive to manufacture and may be printed on the inside of an enclosure for the IDDB system 100 situated away from the skin of the patient to minimize absorption. The transceiver 220 may also include a wired transceiver interface, e.g., a USB port or other type of wired connection, for communication with one or more other devices over a LAN, MAN and/or WAN.

The IDDB system 100 further includes a biosensor 200 and drug delivery system 210. The biosensor 200 includes one or more types of sensors, such as a PPG circuit 110, a temperature sensor 112 or an activity monitoring circuit 114. The temperature sensor 112 is configured to detect a temperature of a patient. For example, the temperature sensor 112 may include an array of sensors (e.g., 16×16 pixels) positioned on a side of the biosensor 200 such that the array of sensors are adjacent to the skin of the patient. The array of sensors then detects an indication of the temperature of the patient from the skin.

The activity monitoring circuit 114 is configured to monitor the activity level of the patient. For example, the activity monitoring circuit 114 may include a multiple axes accelerometer that measures a position of the patient and motion of the patient. In one aspect, the activity monitoring circuit 114 determines periods of activity and rest. For example, the activity monitoring circuit 114 monitors and records periods of rest that meet a predetermined threshold of low motion or activity level, such as sitting, lying, sleeping, etc. The activity monitoring circuit 114 may also monitor and record periods of activity that meet a predetermined threshold of motion or activity level, such as walking, running, lifting, squatting, etc. The biosensor 200 is then configured to measure and store the patient vitals with an indicator of the activity level of the patient. For example, blood oxygen levels may vary greatly in patients with COPD during rest and activity. The vitals of the patient are tracked during periods of activity and rest and the level of activity at time of measuring the vitals is recorded. The biosensor 200 is thus configured to associate measurements of patient vitals with the activity level of the patient.

In another aspect, to help lower power consumption, in an embodiment, the IDDB system 100 includes a rest mode. For example, the activity monitoring circuit 114 may signal a rest mode when a patient is asleep or meets a predetermined threshold of low activity level for a predetermined time period. In the rest mode, the IDDB system 100 signals one or more modules to halt non-essential processing functions. When the activity monitoring circuit 114 detects a higher activity level exceeding another predetermined threshold for a predetermined time period, the the IDDB system 100 signals one or more modules to exit rest mode and resume normal functions. This activity monitoring feature helps to save power and extend battery life of the IDDB system 100.

In another aspect, the activity monitoring circuit is configured to include a fitness tracker application. The activity monitoring circuit 114 may monitor a number of steps of the patient, amount and length of periods of sleep, amount and length of periods of rest, amount and length of periods of activity, etc.

The biosensor 200 also includes a PPG circuit 110. The PPG circuit 110 may be configured to detect oxygen saturation ($SaO_2$ or $SpO_2$) levels in blood flow, as well as heart rate and blood pressure. In addition, the PPG circuit 110 is configured to detect concentration levels or indicators of one or more substances in the blood flow of the patient as described in more detail herein.

The IDDB system 100 also includes the integrated drug delivery system 210. The drug delivery system 210 is configured to deliver a dosage of medication at a rate of administration and at a scheduled time. In one aspect, the drug delivery system 210 includes an integrated drug receptacle 102 though an external source of medication may also be employed. In another aspect, the drug delivery system 210 includes a fuel cell 104, one or more needles 106 and tubing 108 connecting the drug receptacle 102 to the needles 106. The fuel cell 104 releases a predetermined amount of fuel, such as hydrogen, to pressurize the tubing 108 and force a dosage of medication from the drug receptacle 102 through the needles 106 into the skin. In another aspect, other integrated medication delivery systems 212 may be used to control the dosage of medication, rate of administration of the medication and schedule of administration.

The IDDB system 100 may also include a display 230. The IDDB system 100 may be configured to display a graphical user interface (GUI) that includes biosensor data and drug delivery information.

Embodiment—Needles

Figure 3:
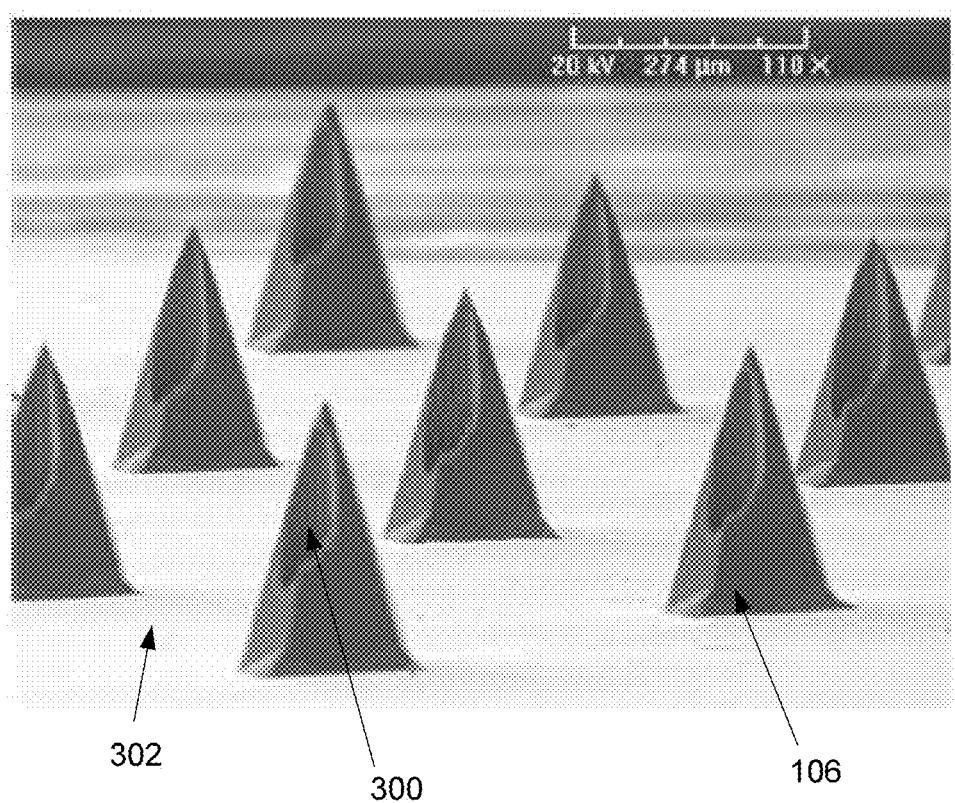
FIG. 3 illustrates an exemplary embodiment of the one or more needles 106 implemented in the IDDB system.

FIG. 3 illustrates an exemplary embodiment of the one or more needles 106 implemented in the IDDB system 100. The needles 106 are positioned to extend from a surface 302 of the IDDB system 100 towards the skin of the patient. The needles 106 are configured to pierce at least the upper epidermal layer of a patient's skin. For example, the needles 106 may include an array or bed of 50 μm bore needles. In another embodiment, the array of needles 106 may have other various sizes or lengths and the openings may vary in size as well depending on the medication and type of injection. Alternatively, one needle 106 may be implemented instead of an array of needles 106, e.g. a single 1.25 mm to 0.4 mm length needle may be implemented or a 2.5 mm needle that pierces the subcutaneous fat layer. In use, the medication flows through the bores 300 or openings in the one or more needles 106 into the skin.

In another embodiment, the needles or a coating over the needles 106 may be electrochemically doped with medication. The needles 106 are then stimulated with an AC and/or DC electric current to release the medication. The applied electrical current may be varied to control the dosage of medication and rate of administration of the medication.

In another embodiment, one or more of the needles 106 include coatings to react with targeted biomarkers. For example, a first needle 106 may include a coating with an enzyme that reacts in the presence of glucose while a second needle 106 includes a coating that reacts in the presence of another targeted biomarker. In use, the needles 106 are electrically stimulated using an AC and/or DC current. The coatings of the needles 106 may then change impedance or provide another different electrical or chemical signature based on the presence and concentration of the targeted biomarker.

Embodiment—Drug Delivery System

Figure 4:
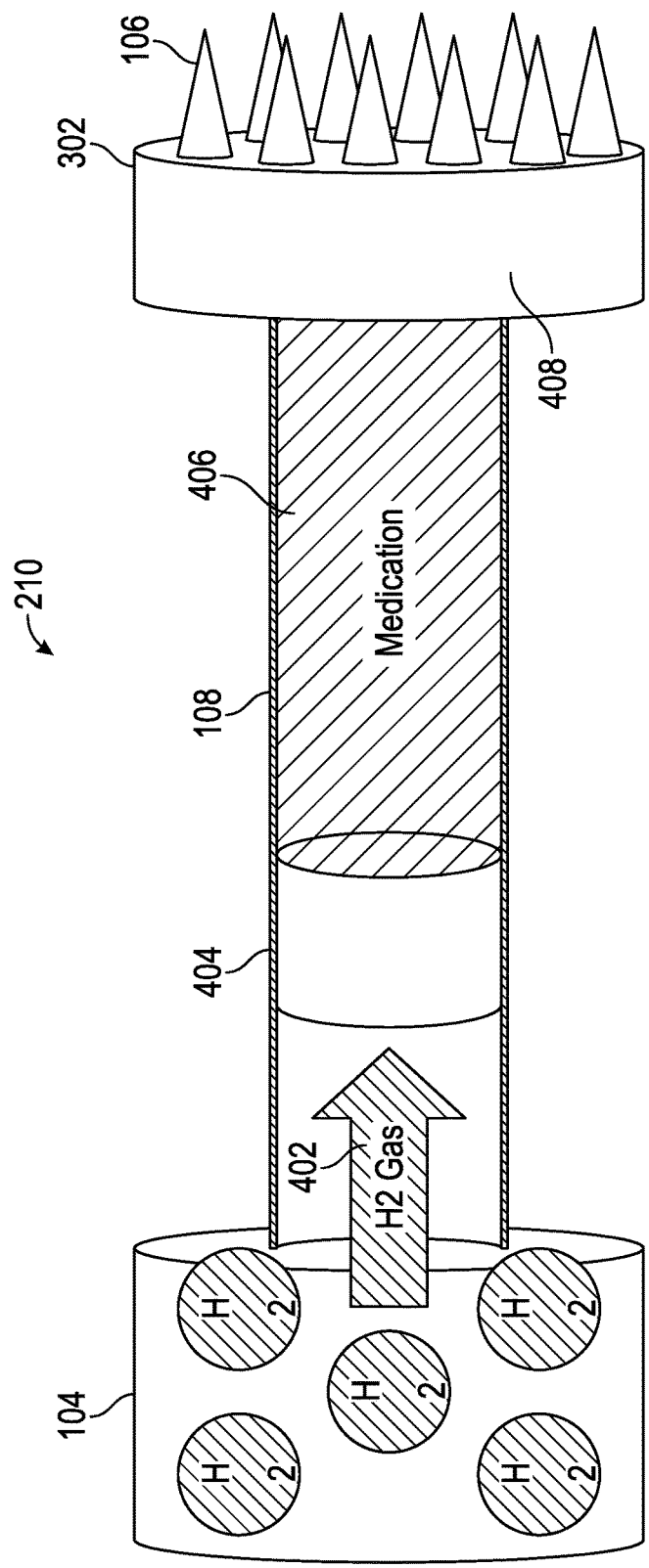
FIG. 4 illustrates a schematic block diagram of an exemplary embodiment of the drug delivery system integrated in the IDDB system.

FIG. 4 illustrates a schematic block diagram of an exemplary embodiment of the drug delivery system 210 integrated in the IDDB system 100. The exemplary drug delivery system 210 includes a fuel cell 104, in this example an $H_2$ fuel cell, coupled to flexible tubing 108. A stopper or bumper 404, such as a rubber or other material plug, is moveably positioned within the tubing to provide an air tight seal between the fuel cell 104 and the medication 406. The fuel cell 104 releases the fuel ($H_2$ gas) 402. The fuel 402 exerts pressure on the stopper 404 and pushes the medication 406 through the tubing 108 and into the needles 106. For example, in an embodiment, a dosage of 1 cc of medication may be injected into the skin using a bed of 50 μm bore micro-needles 106. The IDDB system 100 is configured to control the dosage and dosing rate of the medication by controlling the release of the fuel $H_2$ gas 402. For example, the fuel cell 194 releases the fuel 402 under the control of the processing circuit 202 in order to exert a pressure configured to administer a predetermined dosage at a predetermined dosage rate. The tubing 108 and/or the rubber stopper 404 may be manufactured from durable Silicone, EPDM, Neoprene and/or natural Pure Gum rubber.

The medication 406 may be stored in the drug receptacle 102 and/or tubing 108. The receptacle 102 includes an interface 408 with the needles 106, e.g. with a one way valve, for flow of medication into the bores of the needles 106. For example, the rubber stomper 404 is situated between Port A 130*a* and Port B 130*b* (shown in FIG. 1)

within the tubing. The fuel cell 104 releases $H_2$ gas 402 through Port A 130a into the tubing 108. The $H_2$ gas 402 pushes the stomper 404 in the tubing 108 and pressurizes the medication 406 in the tubing 108 and drug receptacle 102. This pressure forces the medication 406 through the bores 300 of the needles 106.

Though an $H_2$ fuel cell 104 is described herein, other valve or pump mechanisms may alternatively be implemented for dispensing medication through the needles 106 in the IDDB system 100. For example, an air pump or electrically controlled syringe mechanism or atomizing spray pump may be implemented alternatively or in addition to the mechanisms described herein.

Additional medication 406 may be added to the drug receptacle 102, e.g. through Port B 130b or through an additional opening into the drug receptacle 102. Alternatively, an IV catheter may be coupled to the drug delivery system 210, e.g. through Port B 130b, to administer medication 406 through the one or more needles 106. Depending on the type of medication 406, the fuel cell 104 may be implemented to release $H_2$ fuel 402 and force the medication 406 from the catheter of the IV system into the one or more needles 106.

Embodiment—Needle Sensing System

Figure 5:
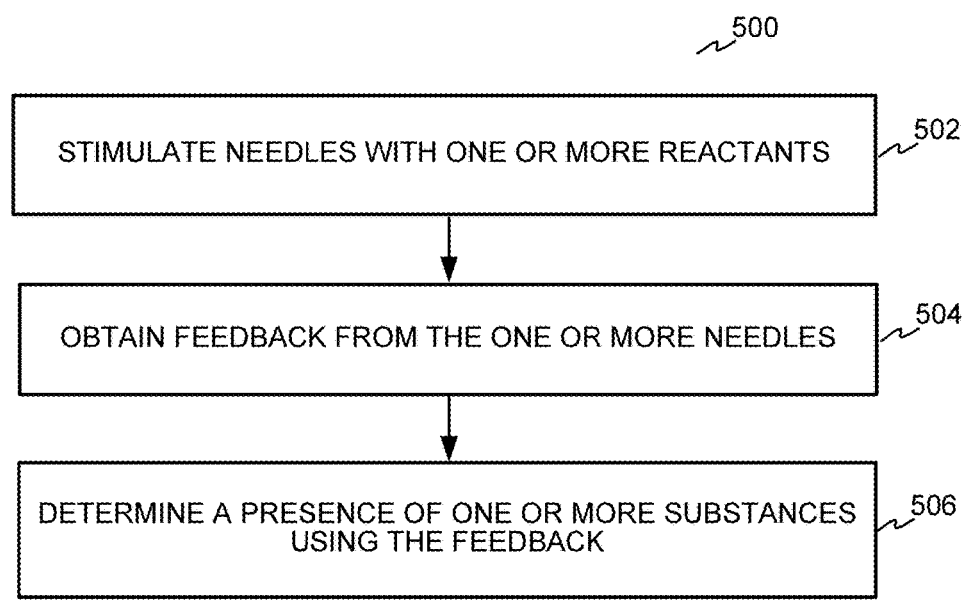
FIG. 5 illustrates a logical flow diagram of an embodiment of a method for a needle sensing system.

FIG. 5 illustrates a logical flow diagram of an embodiment of a method 500 for a needle sensing system. In an embodiment, one or more of the individual needles 106 include a coating with a reactant that reacts in the presence of a targeted biomarker, such as glucose, NACL or other substance. Alternatively to use of coatings, the needles 106 may be formed or manufactured from one or more materials doped with a reactant that reacts with one or more targeted biomarkers. For example, at least one needle may include a coating with an enzyme that reacts in the presence of glucose. In addition, one or more other needles 106 may include different coatings that react with different targeted biomarkers.

In use, the IDDB system 100 is configured to electrically stimulate the needles 106 using an AC and/or DC current at 502 and measure any feedback at 504. For example, the reactant in the coatings of the needles 106 may change impedance or provide another different electrical or chemical response based on the presence and concentration of the targeted biomarker. The IDDB system 100 analyzes the feedback and determines the presence and concentration of the targeted biomarker from the reaction at 506.

Embodiment—ECG System

In another embodiment, the IDDB system 100 includes an ECG system wherein a plurality of the individual needles 106 include electrodes to detect Electrocardiography (ECG) measurements. The electrodes in the needles 106 detect the electrical charges at multiple locations through the patient's skin that arise from the heart's pattern of depolarizing during each heartbeat. An array or bed of needles 106 may be placed at different location on a single patch to better determine the magnitude and direction of the heart's electrical depolarization through the cardiac cycle. Alternatively, multiple patches may be used in different locations to determine the ECG. The differences in voltage measured by the electrodes in the needles 106 at the various locations are correlated to generate the electrocardiogram. The ECG can be used to measure the heart rate and rhythm of heartbeats of the patient.

Embodiment—Wireless Patch with Interchangeable Connector Leads

Figure 6:
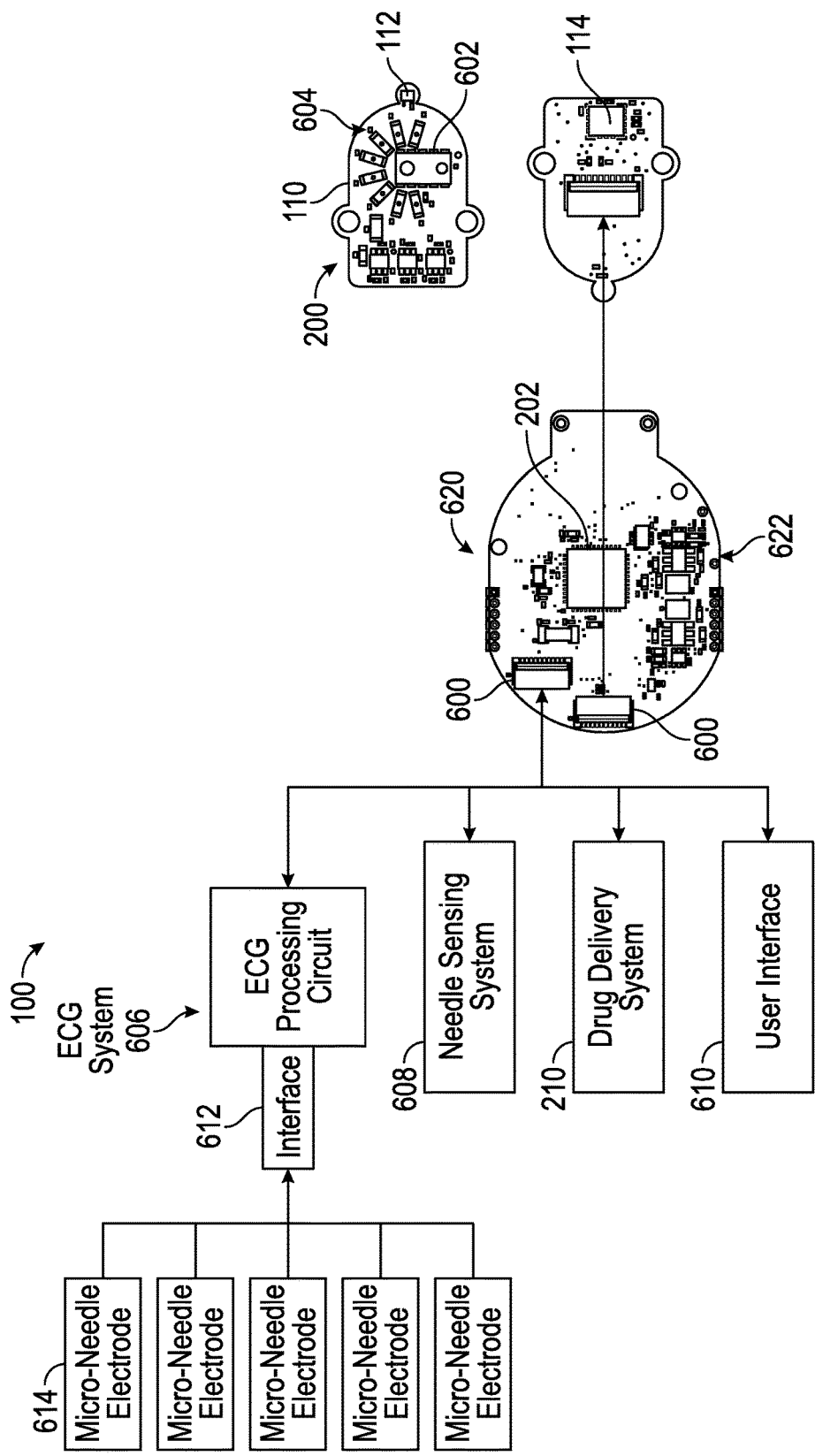
FIG. 6 illustrates an exemplary embodiment of the IDDB system having a processing circuit with interchangeable connector leads.

FIG. 6 illustrates an exemplary embodiment of the IDDB system 100 having a processing circuit 202 with interchangeable connector leads 600. The IDDB system 100 includes a wireless patch 602 having a wireless transceiver 118 coupled to a printed circuit board (PCB) 622. The PCB 622 includes at least one processing circuit 202 coupled to a plurality of connector leads 600. In an embodiment, the connector leads 600 have a common interface for interchangeability of modules. For example, the connector leads 600 may interface with one or more types of devices desired for use with the wireless patch 620. Though only two interfaces 600 are illustrated in FIG. 6, additional connector leads 600 may be implemented.

In one aspect, one of the plurality of connector leads 600 is coupled to the biosensor 200. In the example shown in this figure, the bio sensor 200 includes the PPG circuit 110, the temperature sensor 112 and activity module 114. The biosensor 200 further includes a photodetector circuit 602 and a plurality of LEDs 604 explained in more detail herein.

In another aspect, one of the plurality of connector leads 600 is coupled to the drug delivery system 210. In another aspect, one of the plurality of connector leads 600 is coupled to the ECG system 606. The ECG system 606 includes an ECG processing circuit 616, an interface (such as a 3.5 mm jack) 612, and the plurality of needle electrodes 614. The ECG processing circuit 616, e.g., determines the differences in voltage measured by the needle electrodes 614 at the various locations of the patient and may also correlate the measurements to generate the electrocardiogram. The electrocardiogram is then wirelessly transmitted to a monitoring device by the wireless transmitter 118. In another embodiment, the monitoring device may determine the electrocardiogram based on information from the ECG processing circuit 616.

In another aspect, one of the plurality of connector leads 600 is coupled to the needle sensing system 608. The needle sensing system 608 includes a processing circuit and interfaces with one or more of the needles 106 that include coatings to react with one or more targeted biomarkers. The processing circuit for the needle sensing system 608 controls the stimulation of the needles 106 using an AC and/or DC current and determines a presence or concentration of the targeted biomarker based on the feedback.

In another aspect, one of the plurality of connector leads 600 is coupled to a user interface 610. The user interface 610 may wirelessly communicate with a user device. For example, the user interface may transmit data and information from the IDDB system 100, such as the historical and real-time biosensor data of the patient, dosage history, etc.

The wireless patch 620 may thus be coupled to a combination of one or more of: the biosensor 200, the drug delivery system 210, the ECG system 606, the needle sensing system 608, the user interface 610, or other device/module.

Embodiment—IDDB System Form Factors

Figure 7A:
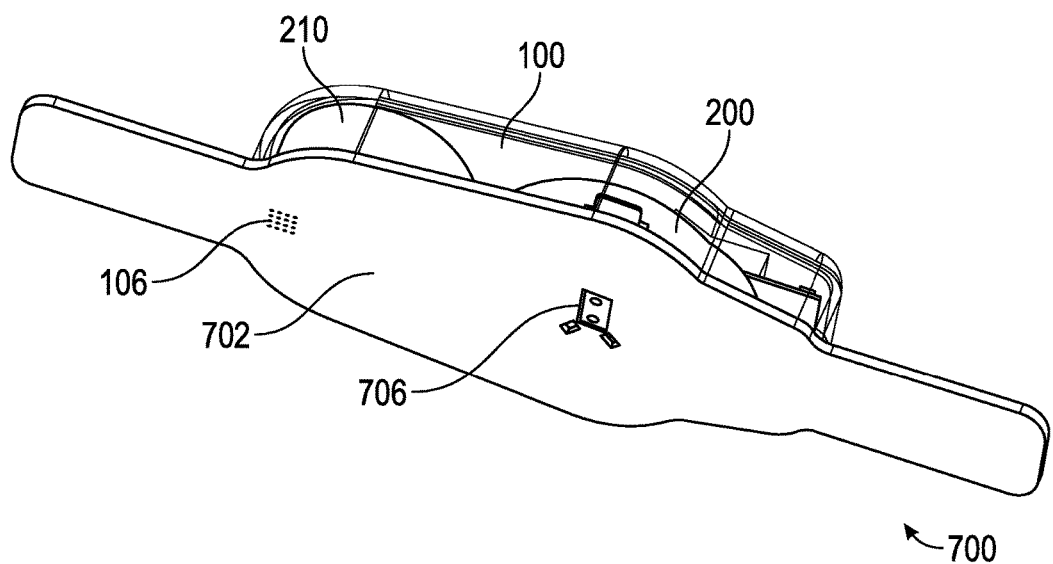
FIG. 7A illustrates a perspective view of an exemplary embodiment of a form factor of the IDDB system.

FIG. 7A illustrates a perspective view of an exemplary embodiment of a form factor of the IDDB system 100. In an embodiment, the IDDB system 100 is implemented on a wearable patch 700. The wearable patch 700 may include an adhesive backing 702 to attach to the skin of a patient, such as on a hand, arm, wrist, forehead, chest, abdominal area, or other area of the skin or body or living tissue. Alternatively, the wearable patch 700 may be attached to the skin using adhesive tape. In general, the wearable patch 700 should be secured such that an aperture 706 for the biosensor and the needles 106 are positioned against the skin.

Figure 7B:
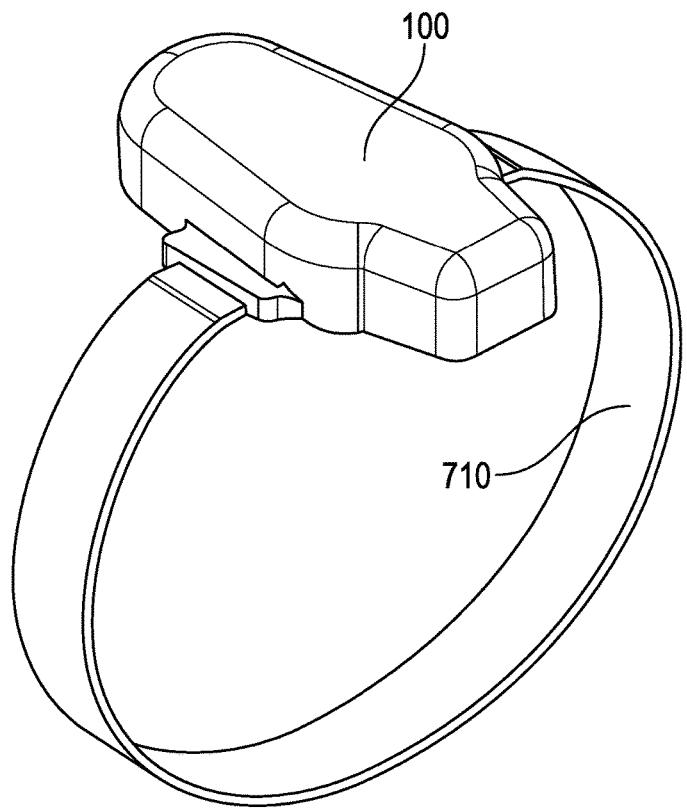
FIG. 7B illustrates a perspective view of an exemplary embodiment of another form factor of the IDDB system.

FIG. 7B illustrates a perspective view of an exemplary embodiment of another form factor of the IDDB system 100. In another embodiment, the IDDB system 100 is implemented on an arm band 710. The arm band 710 may be configured with an adjustable band for placement on an arm, the wrist, on one or more fingers, around a leg, etc. In general, the arm band 700 should be secured such that an aperture 706 for the biosensor and the needles 106 are positioned against the skin.

Figure 8A:
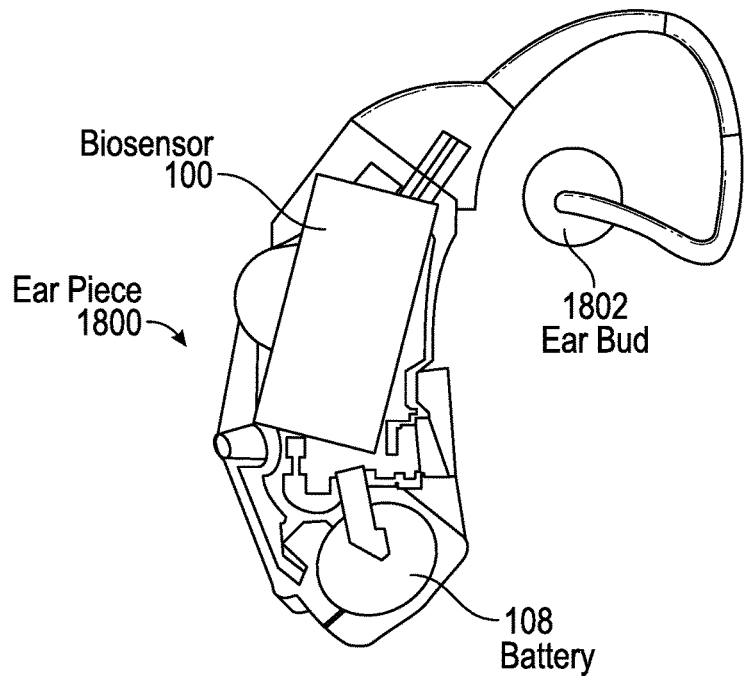
FIG. 8A illustrates a perspective view of an exemplary embodiment of another form factor of the IDDB system.

FIG. 8A illustrates a perspective view of an exemplary embodiment of another form factor of the IDDB system 100. In this embodiment, the IDDB system 100 is configured in an earpiece 800. The earpiece 800 includes an earbud 802. The biosensor 200 is configured to transmit light into the ear canal from one or more optical fibers in the ear bud 1802 and detect light from the ear canal using the one or more optical fibers.

Figure 8B:
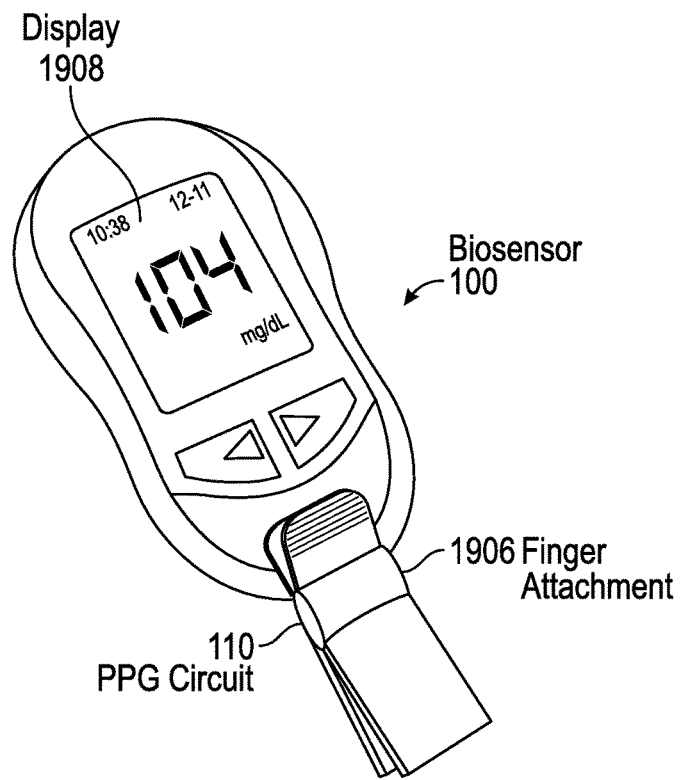
FIG. 8B illustrates a perspective view of an exemplary embodiment of another form factor of the IDDB system.

FIG. 8B illustrates a perspective view of an exemplary embodiment of another form factor of the IDDB system 100. In this embodiment, the IDDB system 100 is configured to attach to a finger or fingertip using finger attachment 806. The finger attachment 806 includes the PPG circuit 110 and the drug delivery system 210. The finger attachment 806 is configured to securely hold a finger that is inserted into the finger attachment 806. The finger attachment 806 may be implemented within the same encasement as the other components of the IDDB system 100 or be communicatively coupled either through a wired or wireless interface to the other components of the IDDB system 100. A display 804 is implemented for the IDDB system 100 with a graphical user interface (GUI) that displays biosensor data and dosage information.

The IDDB system 100 may be configured to be attached to an ear lobe or to a fingertip. Various other form factors may be implemented as well. In addition, one or more IDDB system 100s in one or more form factors may be used in combination to determine biosensor data and/or administer medications at one or more areas of the body.

Embodiment—Bio-Feedback of Biosensor Data Using IDDB System 100

Figure 9:
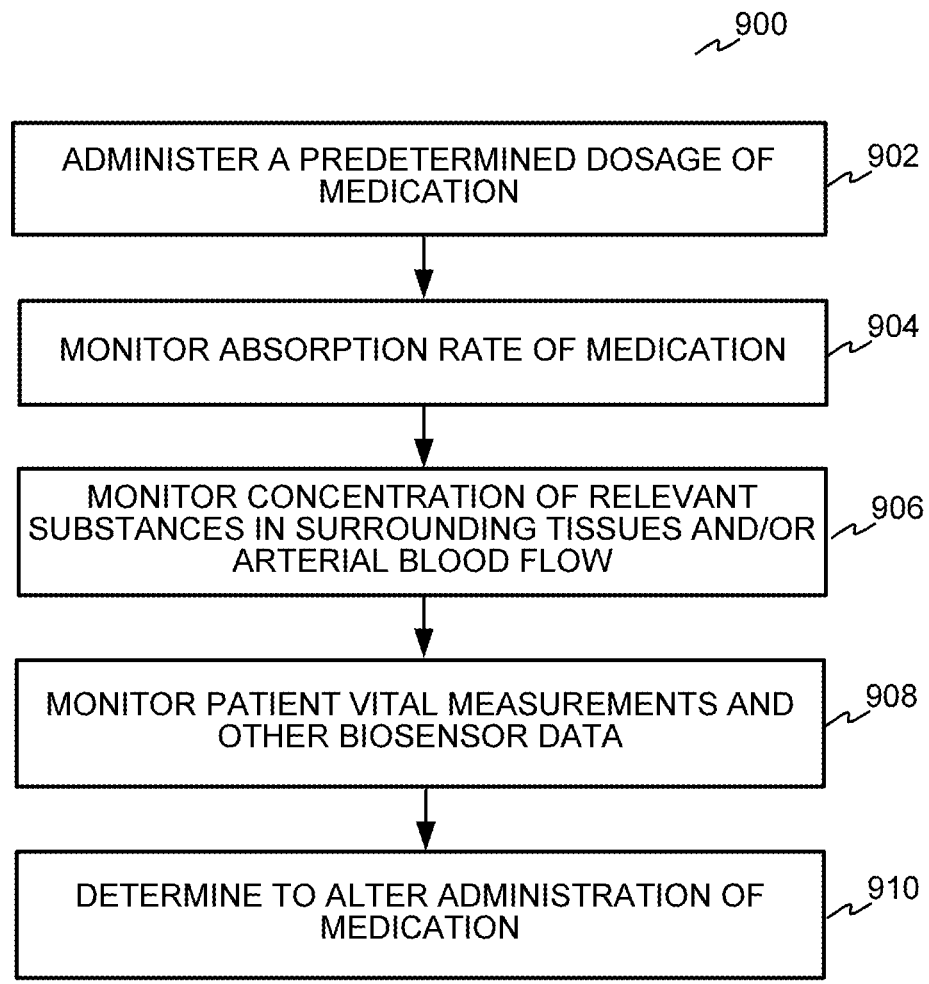
FIG. 9 illustrates a logical flow diagram of an embodiment of a method of the IDDB system.

FIG. 9 illustrates a logical flow diagram of an embodiment of a method 900 of the IDDB system 100. The optimal dosage of a medication is the dosage that gives the desired effect with minimum side effects. The IDDB system 100 may provide feedback of biosensor data, such as absorption rate of the medication and patient vital information, related to the efficacy of the medication to determine more optimal dosages.

In an embodiment, the IDDB system 100 administers a predetermined dosage of medication to the patient's skin at a predetermined rate at 902. During administration and thereafter, the IDDB system 100 non-invasively and continuously monitors the absorption rate of the medication by the skin and surrounding tissue at 904. For example, one or more optical fibers situated in one or more of the needles 106 detect reflected light from the skin and surrounding tissue. The PPG circuit 110 detects a spectral response of the reflected light. The spectral response is analyzed to determine a concentration level of the medication on and/or in the epidermis layer of the skin and surrounding tissue. Over time, the cells of the skin absorb the medication, e.g. into cells of the surrounding tissues at lower levels of the dermis and hypodermis, which include blood vessels. The medication is absorbed into cells of the skin and the surrounding tissue and into the blood vessels. The spectral response of the reflected light is continuously analyzed, e.g. multiple times per second, to monitor the concentration of the medication as it decreases due to the absorption. The absorption rate over time of the medication may thus be determined.

The IDDB system 100 may also non-invasively and continuously monitor concentration of relevant substances in surrounding tissues and arterial blood flow at 906. For example, the PPG circuit 110 using PPG or spectroscopy techniques described herein, detects a spectral response of reflected light at one or more wavelengths. Based on the spectral response, concentration of a substance in the surrounding tissues or arterial blood flow may be determined. The concentration of the medication in the arterial blood flow may be determined or the concentration of a related, relevant substance in the arterial blood flow may be determined. For example, administration of an antibiotic may affect a number of white blood cells in the arterial blood flow. So the concentration of the antibiotic and/or white blood cells may be monitored in the arterial blood flow by the PPG circuit 110. In another example, administration of insulin affects glucose levels in the arterial blood flow. So the absorption rate of insulin into the skin and surrounding tissues is monitored as well as insulin levels or blood glucose levels in the arterial blood flow by the PPG circuit 110.

The IDDB system 100 may also monitor patient vitals, such as respiratory rate, temperature, heart rate, blood pressure, blood oxygen $SPO_2$ levels, ECG, etc. The IDDB system 100 may also monitor other biosensor data, such as activity level, of the patient at 908.

In response to the biosensor data, the IDDB system 100 may determine to alter administration of the medication at 910. For example, the IDDB system 100 may determine to alter one or more of a dosage of the medication, administration rate of the medication, frequency of dosages of the medication, etc. The IDDB system 100 may determine to halt the administration of a dosage or further dosages based on the biosensor data, e.g. when an allergic reaction is detected. The IDDB system 100 then transmits instructions to the drug delivery system 210 to halt further administration of the medication or otherwise alter administration of the medication. In an embodiment, the biosensor data is provided to a caretaker, such as a physician or pharmacy through a user interface. The caretaker may then instruct the IDDB system 100 to alter administration of medication based on the biosensor data through the user interface.

The IDDB system 100 is thus configured to deliver medication and provide biosensor data, such as absorption rate and patient vital information, related to the efficacy of the medication to determine more optimal dosages.

Embodiment—Administration of Medication Using IDDB System

Figure 10:
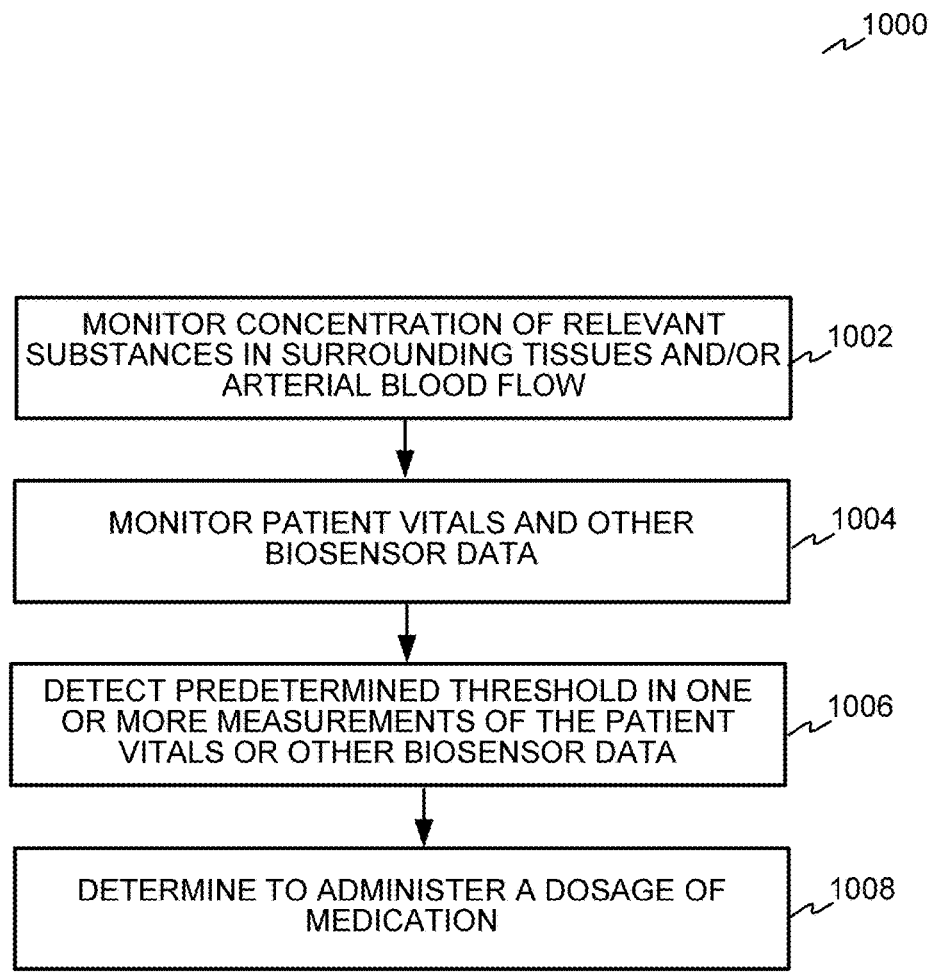
FIG. 10 illustrates a logical flow diagram of an embodiment of a method for administration of medication using the IDDB system

FIG. 10 illustrates a logical flow diagram of an embodiment of a method 1000 for administration of medication using the IDDB system 1000. The IDDB system 100 non-invasively and continuously monitors a concentration of relevant substances in surrounding tissues and/or arterial blood flow at 1002. For example, the PPG circuit 110 using PPG techniques described herein, detects a spectral response of reflected light at one or more wavelengths. Based on the spectral response, concentration levels of one or more relevant substances in surrounding tissues and/or arterial blood flow may be determined. For example, an indicator of insulin levels after caloric intake in arterial blood flow may be determined and monitored or a level of white blood cells may be monitored in the arterial blood flow by the PPG circuit 110.

The IDDB system 100 may also monitor patient vitals, such as respiratory rate, temperature, heart rate, blood pressure, blood oxygen SPO2 levels, ECG, etc. The IDDB system 100 may also monitor other biosensor data, such as activity level, of the patient at 1004. For example, the IDDB system 100 may monitor heart rate, respiratory rate, blood pressure, etc. to determine an allergic reaction in a patient.

Based on the biosensor data, at 1008, the IDDB system 100 may determine to administer a dosage of medication using the drug delivery system 210. For example, the IDDB system 100 may detect a predetermined threshold in one or more measurements of the biosensor data. The IDDB system 100 may then determine a dosage amount, rate of administration and/or frequency of dosages.

For example, the IDDB system 100 may determine insulin levels after caloric intake in arterial blood flow have fallen to a predetermined threshold. The IDDB system 100 may then determine to administer insulin to the patient through the drug delivery system 210. Based on the insulin level, the IDDB system 100 may determine a dosage amount, rate of dosage and frequency of dosages.

In another example, many people have dangerous allergic reactions requiring immediate attention, e.g. food allergy or insect bite allergy. The IDDB system 100 may detect patient vitals indicating a dangerous allergic reaction and determine to administer a dosage of epinephrine. For example, the IDDB system 100 may detect one or more of blood pressure, respiratory rate or heart rate that exceed a predetermined threshold indicating an allergic reaction. The IDDB system 100 would then administer epinephrine or other allergy medication in response to the feedback. The IDDB system 100 may thus replace epi-pens in patients with life threatening allergic reactions. Epi-pens may not be available or may be difficult for a person having an allergic reaction to administer. The IDDB system 100 would automate this administration of life saving medication.

In an embodiment, the biosensor data is provided to a caretaker, such as a physician or pharmacy, through a user interface. The caretaker may then instruct the IDDB system 100 to administer the medication based on the biosensor data through the user interface. For example, the IDDB system 100 may transmit an alert to a physician or nurse when a patient exhibits symptoms of an allergic reaction. The IDDB system 100 may transmit the biosensor data with the alert. The caretaker may then instruct the IDDB system 100 to administer medication based on the biosensor data.

Embodiment—PPG Circuit

Figure 11:
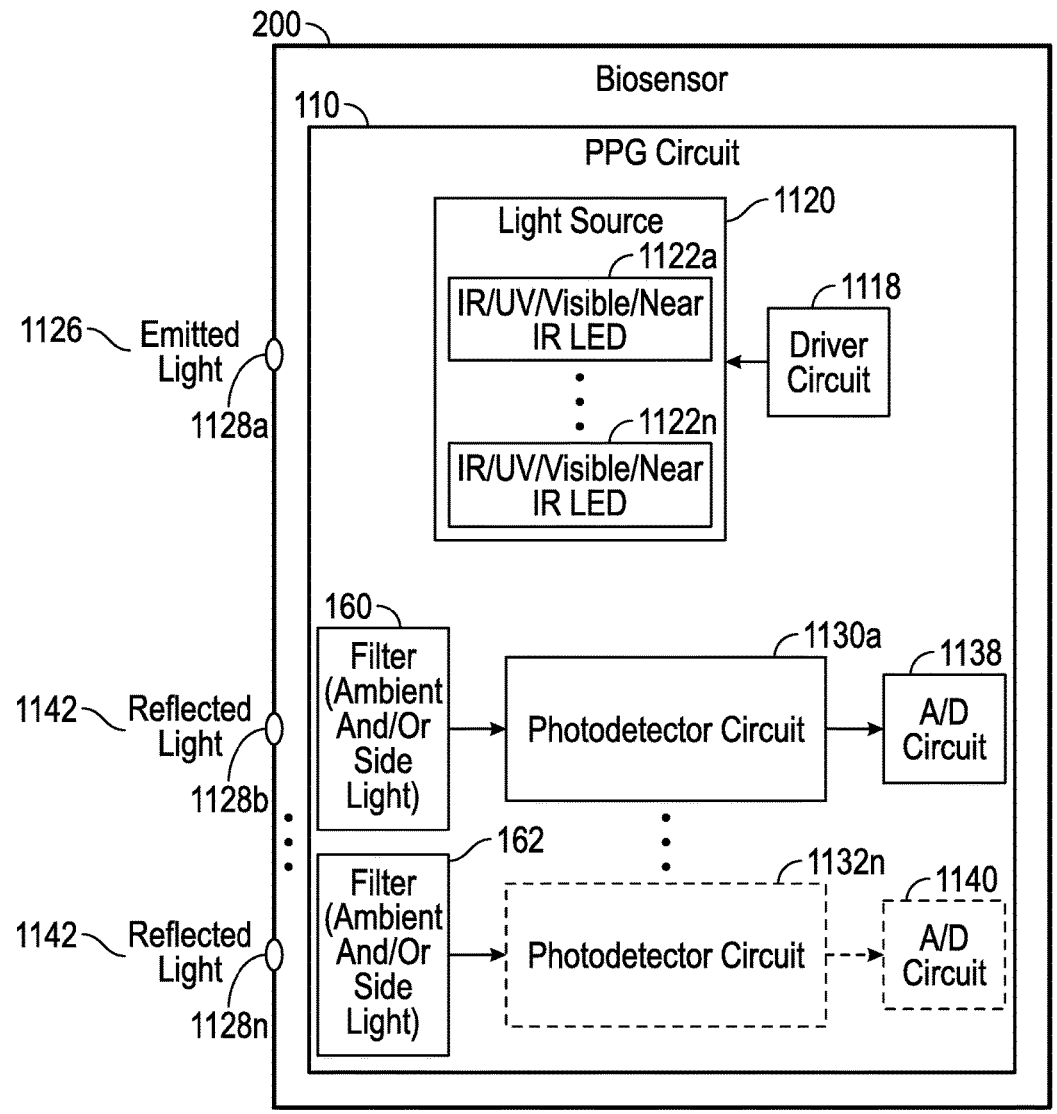
FIG. 11 illustrates a schematic block diagram of an exemplary embodiment of the biosensor illustrating the PPG circuit in more detail.

FIG. 11 illustrates a schematic block diagram of an exemplary embodiment of the biosensor 200 illustrating the PPG circuit 110 in more detail. The PPG circuit 110 implements photoplethysmography (PPG) techniques for obtaining concentration levels or indicators of one or more substances in pulsating arterial blood flow. The PPG circuit 110 includes a light source 1120 having a plurality of light sources, such as LEDs 1122a-n, configured to emit light through at least one aperture 1128a. The PPG circuit 110 is configured to direct the emitted light at an outer or epidermal layer of skin tissue of a patient. The plurality of light sources are configured to emit light in one or more spectrums, including infrared (IR) light, ultraviolet (UV) light, near IR light or visible light, in response to driver circuit 1118. For example, the biosensor 200 may include a first LED 1122a that emits visible light and a second LED 1122b that emits infrared light and a third LED 1122c that emits UV light, etc. In another embodiment, one or more of the light sources 1122a-n may include tunable LEDs or lasers operable to emit light over one or more frequencies or ranges of frequencies or spectrums in response to driver circuit 1118.

In an embodiment, the driver circuit 1118 is configured to control the one or more LEDs 1122a-n to generate light at one or more frequencies for predetermined periods of time.

The driver circuit 1118 may control the LEDs 122a-n to operate concurrently or progressively. The driver circuit 1118 is configured to control a power level, emission period and frequency of emission of the LEDs 1122a-n. The biosensor 200 is thus configured to emit one or more frequencies of light in one or more spectrums that is directed at the surface or epidermal layer of the skin tissue of a patient.

The PPG circuit 110 further includes one or more photodetector circuits 1130a-n. For example, a first photodetector circuit 1130a may be configured to detect visible light and the second photodetector circuit 1130b may be configured to detect IR light. The first photodetector circuit 1130a and the second photodetector circuit 1130b may also include a first filter 1160 and a second filter 1162 configured to filter ambient light and/or scattered light. For example, in some embodiments, only light received at an approximately perpendicular angle to the skin surface of the patient is desired to pass through the filters. The first photodetector circuit 1130 and the second photodetector circuit 1132 are coupled to a first A/D circuit 1138 and a second A/D circuit 1140. The A/D circuits 1138 and 1140 may also include an amplifier and other components needed to generate the spectral response. In another aspect, the plurality of photodetectors 1130 is coupled in parallel to a single amplifier and A/D circuit 1138. The light detected by each of the photodetectors 1130 is thus added and amplified to generate a single spectral response.

In another embodiment, a single photodetector circuit 1130 may be implemented operable to detect light over multiple spectrums or frequency ranges. For example, the photodetector circuit 1130 may include a Digital UV Index/IR/Visible Light Sensor such as Part No. Si1145 from Silicon Labs™.

The one or more photodetector circuits 1130 include a spectrometer or other type of circuit configured to detect an intensity of light as a function of wavelength or frequency to obtain a spectral response. The one or more photodetector circuits 1130 detects the intensity of light either transmitted through or reflected from tissue of a patient that enters one or more apertures 1128b-n of the biosensor 200. For example, the light may be detected from transmissive absorption (e.g., through a fingertip or ear lobe) or from reflection (e.g., reflected from a forehead or stomach tissue). The photodetector circuits 1130 then obtain a spectral response of the detected light by measuring the intensity of light either transmitted or reflected to the photodiodes.

Figure 12:
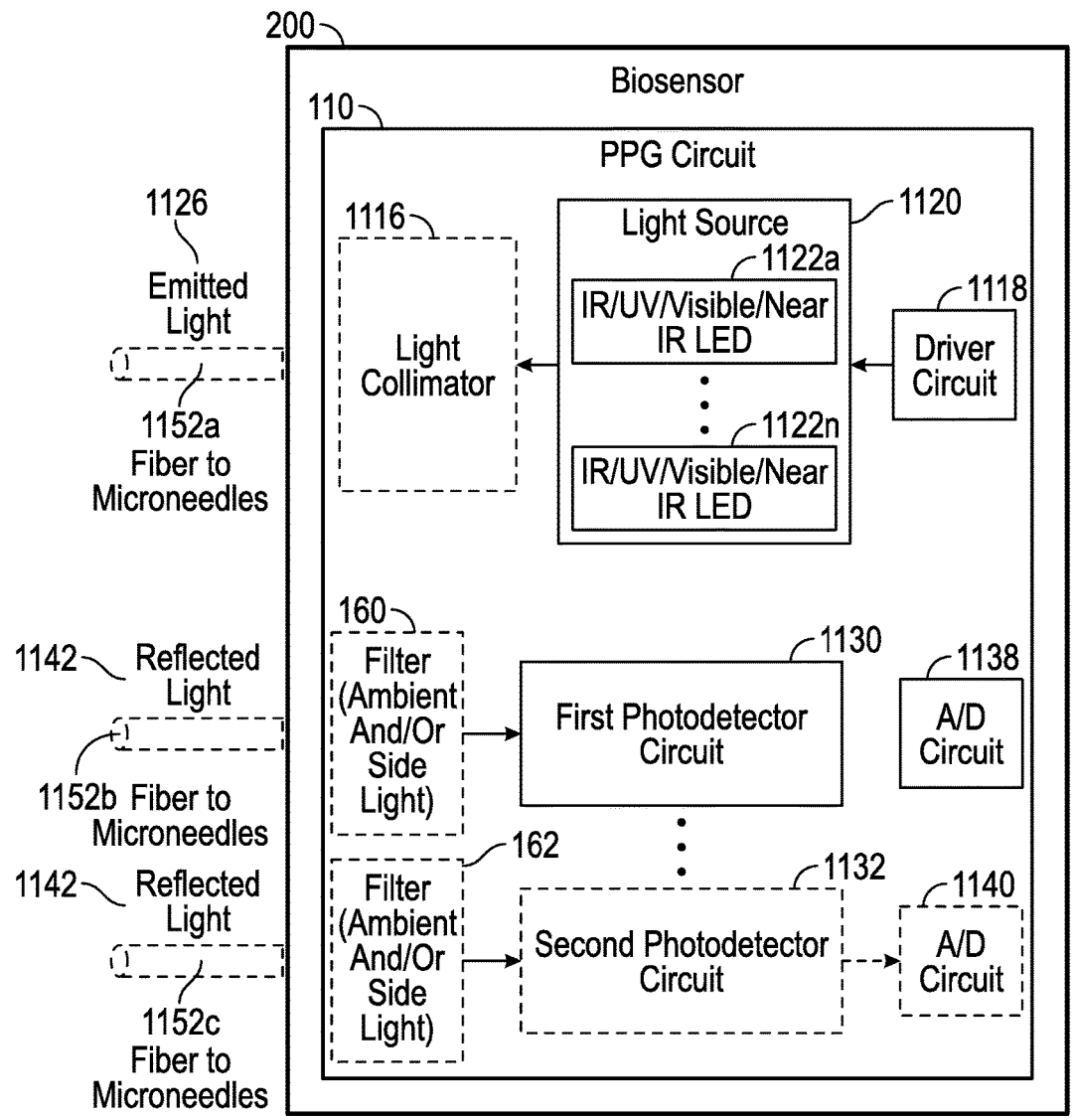
FIG. 12 illustrates a schematic block diagram of another exemplary embodiment of the biosensor illustrating the PPG circuit in more detail.

FIG. 12 illustrates a schematic block diagram of another exemplary embodiment of the biosensor 200 illustrating the PPG circuit 110 in more detail. In this embodiment, the biosensor 200 is configured for emitting and detecting light through fibers situated in one or more needles 106. The PPG circuit 110 is optically coupled to a plurality of optical fibers 1152a-c. In an embodiment, the plurality of optical fibers 1152 includes a first optical fiber 1152a optically coupled to the light source 1120, a second optical fiber 1152b optically coupled to a first photodetector circuit 1130 and a third optical fiber 1152c optically coupled to the second photodetector circuit 1132. Other configurations and numbers of the plurality of optical fibers 1152 may also be implemented. In an aspect, the plurality of optical fibers 1152 is situated within the needles 106 to transmit and detect light through the bores 300 of the needles 106. A light collimator 1116, such as a prism, may be used to align a direction of the light emitted from the light source 1120, e.g. such as light emitted in the visible frequency range. One or more filters 1160 may optionally be implemented to receive the reflected light 1142 from the plurality of optical fibers 1152b, 1152c. However, the filters 1160 may not be needed as the plurality of optical fibers 1152b, 1152c may be sufficient to filter ambient light and/or scattered light.

Embodiment—Concentration of Substances in Arterial Blood Flow

One or more of the embodiments of the biosensor 200 described herein are configured to detect a concentration level or indicator of one or more substances within blood flow, such as analyte levels, nitric oxide levels, insulin resistance or insulin response after caloric intake and predict diabetic risk or diabetic precursors. The biosensor 200 may detect insulin response, vascular health, cardiovascular sensor, cytochrome P450 proteins (e.g. one or more liver enzymes or reactions), digestion phase 1 and 2 or caloric intake. The biosensor 200 may even be configured to detect proteins or other elements or compounds associated with cancer. The biosensor 200 may also detect various electrolytes and many common blood analytic levels, such as bilirubin amount and sodium and potassium. For example, the biosensor 200 may detect sodium NACL concentration levels in the arterial blood flow to determine dehydration. The biosensor 200 may also detect blood alcohol levels in vivo in the arterial blood flow. Because blood flow to the skin can be modulated by multiple other physiological systems, the PPG sensor 110 may also be used to monitor breathing, hypovolemia, and other circulatory conditions. The biosensor 200 may also detect blood pressure, peripheral oxygen (SpO$_2$ or SaO$_2$) saturation, heart rate, respiration rate or other patient vitals. The PPG circuit 110 may also be used to detect sleep apnea based on oxygen saturation levels and activity monitoring during sleep.

In use, the biosensor 200 performs PPG techniques using the PPG circuit 110 to detect the concentration levels of substances in blood flow. In one aspect, the biosensor 200 analyzes reflected visible or IR light to obtain a spectrum response such as, the resonance absorption peaks of the reflected visible, UV or IR light. The spectrum response includes spectral lines that illustrate an intensity or power or energy at a wavelength or range of wavelengths in a spectral region of the detected light.

The ratio of the resonance absorption peaks from two different frequencies can be calculated and based on the Beer-Lambert law used to obtain various levels of substances in the blood flow. First, the spectral response of a substance or substances in the arterial blood flow is determined in a controlled environment, so that an absorption coefficient $\alpha_{g1}$ can be obtained at a first light wavelength $\lambda_1$ and at a second wavelength $\lambda_2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined using the following equations:

At the first wavelength $\lambda_1$, $I_1 = I_{in1} * 10^{-(\alpha_{g1}C_{gw} + \alpha_{w1}C_w) * l}$ At the second wavelength $\lambda_2$, $I_2 = I_{in2} * 10^{-(\alpha_{g2}C_{gw} + \alpha_{w2}C_w) * l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$ $\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood Then letting R equal:

$$R = \frac{\log 10\left(\frac{I1}{Iin1}\right)}{\log 10\left(\frac{I2}{Iin2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2}) * R - (\alpha_{w1} - \alpha_{gw1})}$$

The biosensor 200 may thus determine the concentration of various substances in arterial blood using spectroscopy at two different wavelengths using Beer-Lambert principles.

The biosensor 200 determines concentration of one or more substances using Beer-Lambert principles. The biosensor 200 transmits light at least at a first predetermined wavelength and at a second predetermined wavelength. The biosensor 200 detects the light (reflected from the skin or transmitted through the skin) and analyzes the spectral response at the first and second wavelengths to detect an indicator or concentration level of one or more substances in the arterial blood flow. In general, the first predetermined wavelength is selected that has a high absorption coefficient for the targeted substance while the second predetermined wavelength is selected that has a low absorption coefficient for the targeted substance. Thus, it is generally desired that the spectral response for the first predetermined wavelength have a higher intensity level than the spectral response for the second predetermined wavelength.

In another aspect, the biosensor 200 may transmit light at the first predetermined wavelength and in a range of approximately 1 nm to 50 nm around the first predetermined wavelength. Similarly, the biosensor 200 may transmit light at the second predetermined wavelength and in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted light by the target substance may by spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated. The biosensor 200 analyzes the first and second spectral responses to detect an indicator or concentration level of one or more substances in the arterial blood flow at 406.

Photoplethysmography (PPG) is used to measure time-dependent volumetric properties of blood in blood vessels due to the cardiac cycle. For example, the heartbeat affects volume of arterial blood flow and the concentration of absorption levels being measured in the arterial blood flow. Over a cardiac cycle, pulsating arterial blood changes the volume of blood flow in an artery. Incident light $I_O$ is directed at a tissue site and a certain amount of light is reflected or transmitted and a certain amount of light is absorbed. At a peak of arterial blood flow or arterial volume, the reflected/transmitted light $I_L$ is at a minimum due to absorption by the venous blood, nonpulsating arterial blood, pulsating arterial blood, other tissue, etc. At a minimum of arterial blood flow or arterial volume during the cardiac cycle, the transmitted/reflected light $I_H$ is at a maximum due to lack of absorption from the pulsating arterial blood.

The biosensor 200 is configured to filter the reflected/transmitted light $I_L$ of the pulsating arterial blood from the transmitted/reflected light $I_H$. This filtering isolates the light due to reflection/transmission of substances in the pulsating arterial blood from the light due to reflection/transmission from venous (or capillary) blood, other tissues, etc. The biosensor 200 may then measure the concentration levels of one or more substances from the reflected/transmitted light $I_L$ in the pulsating arterial blood. Though the above has been described with respect to arterial blood flow, the same principles described herein may be applied to venous blood flow.

In general, the relative magnitudes of the AC and DC contributions to the reflected/transmitted light signal I may be used to substantially determine the differences between the diastolic time and the systolic points. In this case, the difference between the reflected light $I_L$ and reflected light $I_H$ corresponds to the AC contribution of the reflected light (e.g. due to the pulsating arterial blood flow). A difference function may thus be computed to determine the relative magnitudes of the AC and DC components of the reflected light I to determine the magnitude of the reflected light $I_L$ due to the pulsating arterial blood. The described techniques herein for determining the relative magnitudes of the AC and DC contributions is not intended as limiting. It will be appreciated that other methods may be employed to isolate or otherwise determine the relative magnitude of the light $I_L$ due to pulsating arterial blood flow.

Figure 13:
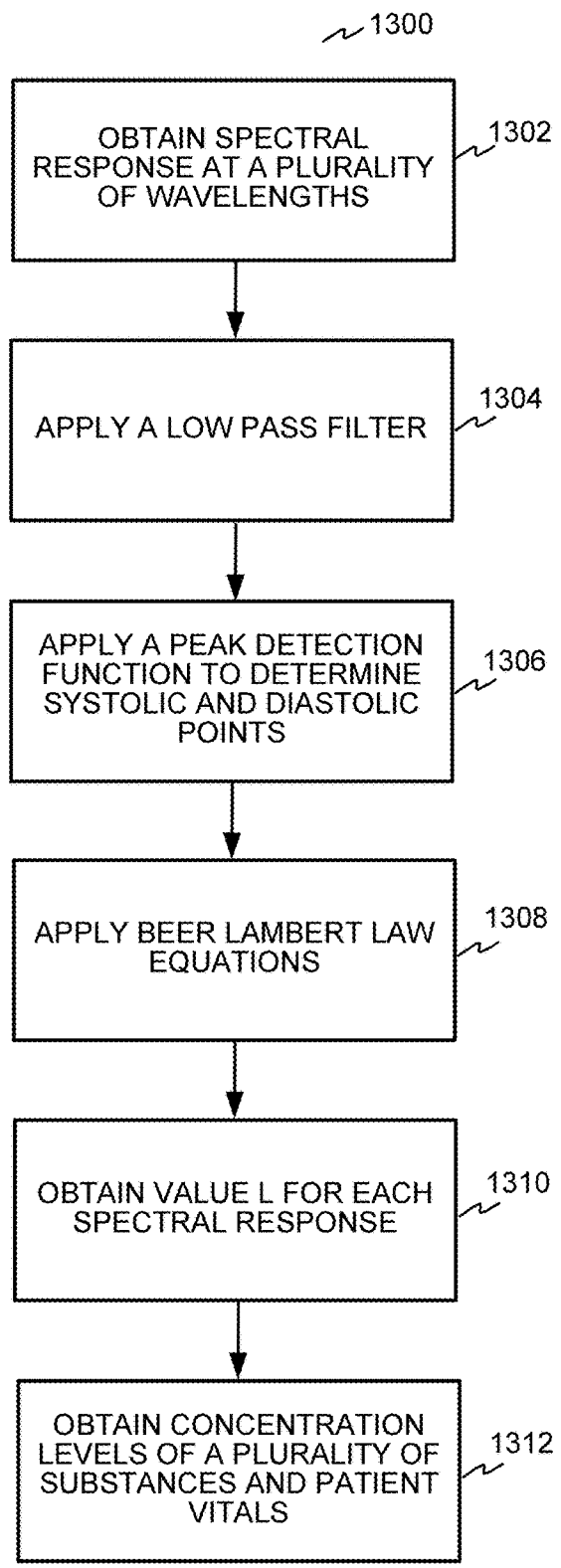
FIG. 13 illustrates a logical flow diagram of an embodiment of a method of the biosensor.

FIG. 13 illustrates a logical flow diagram of an embodiment of a method 1300 of the biosensor 200. In one aspect, the biosensor 200 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially at each predetermined wavelength. In another aspect, light may be pulsed in a wavelength range of 1 nm to 50 nm around each of the predetermined wavelengths. Then, the spectral responses are obtained for the plurality of wavelengths at 1302. The spectral response may be measured over a predetermined period (such as 300 usec.). This measurement process is repeated sequentially pulsing the light and obtaining spectral measurements over a desired measurement period, e.g. from 1-2 seconds to 1-2 minutes or 2-3 hours or continuously over days or weeks. Because the human pulse is typically on the order of magnitude of one 1 HZ, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period.

A low pass filter (such as a 5 Hz low pass filter) is applied to the spectral response signal at 1304. The relative contributions of the AC and DC components are obtained $I_{AC+DC}$ and $I_{AC}$. A peak detection algorithm is applied to determine the systolic and diastolic points at 1306. Beer Lambert equations are applied as described below at 1308. For example, the $L_\lambda$ values are then calculated for one or more of the wavelengths λ at 1310, wherein the $L_\lambda$ values for a wavelength equals:

$$L_\lambda = \text{Log}10\left(\frac{I\text{AC} + \text{DC}}{I\text{DC}}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response.

A ratio R of the $L_\lambda$ values at two wavelengths may then be determined. For example, $$\text{Ratio } R = \frac{L\lambda 1}{L\lambda 2}$$

The $L_\lambda$ values and Ratio R may be determined for one or more of the predetermined measurement periods over a desired time period, e.g. from 1-2 seconds to 1-2 minutes or 2-3 hours or continuously over days or weeks to monitor the values. The $L_\lambda$ values and Ratio R may be used to determine concentration levels of one or more substances in the arterial blood flow as well as patient vitals, such as oxygen saturation SpO2, heart rate, respiration rate, etc. at 1312.

The biosensor 200 may analyze a plurality of wavelengths to determine the concentration of one or more substances. In one aspect, the light source 1120 includes a broad spectrum light source, such as a white light to infrared (IR) or near IR light source, that emits light with wavelengths from e.g. 350 nm to 2500 nm. For example, a broadband tungsten light source for spectroscopy may be used. The spectral response of the reflected light is then measured across the wavelengths in the broad spectrum, e.g. from 350 nm to 2500 nm, concurrently. In an aspect, a charge coupled device (CCD) spectrometer 1030 may be configured to measure the spectral response of the reflected light. The spectral response of the reflected light is analyzed at the plurality of wavelengths, e.g. at 1 nm to 1.5 nm to 2 nm, incremental wavelengths across the wavelengths from 350 nm to 2500 nm. In another embodiment, the spectral response of the reflected light is analyzed for a set of predetermined wavelengths.

In another aspect, the plurality of LEDs 1122a-n emit light at a plurality of wavelengths. The spectral response of the reflected light is analyzed for a set of predetermined wavelengths.

Figure 14:
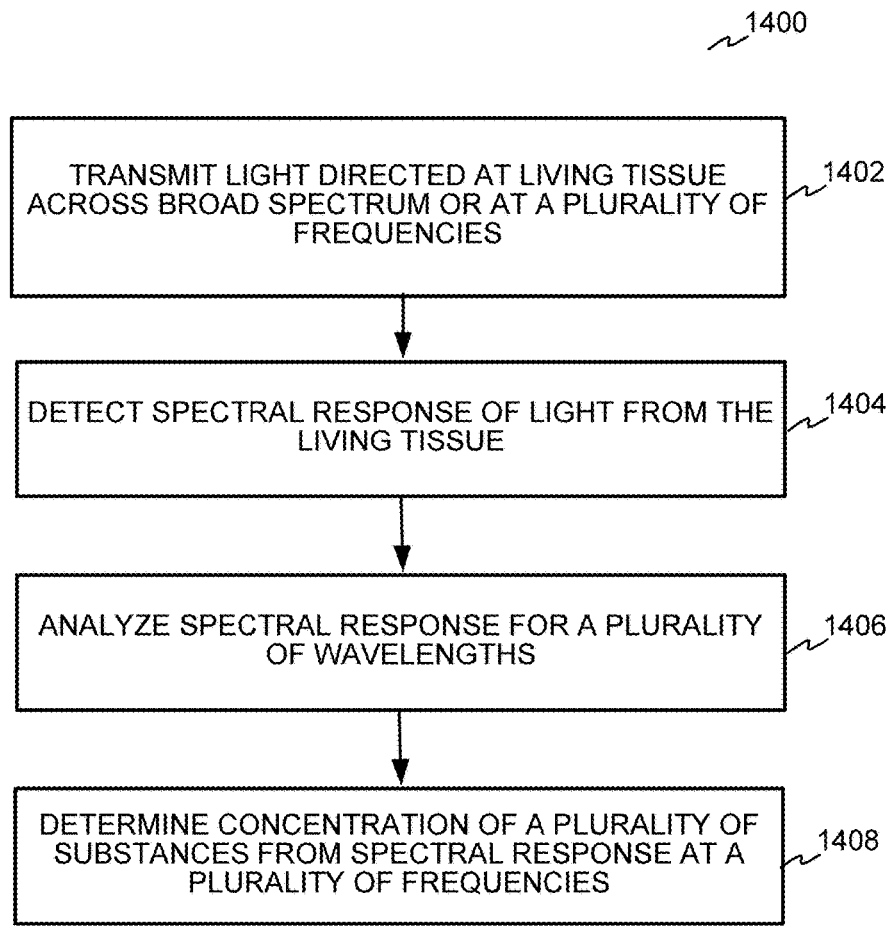
FIG. 14 illustrates a logical flow diagram of an exemplary method to determine blood concentration levels of a plurality of substances using the spectral response for a plurality of wavelengths.

FIG. 14 illustrates a logical flow diagram of an exemplary method 1400 to determine blood concentration levels of a plurality of substances using the spectral response for a plurality of wavelengths. The biosensor 100 transmits light directed at living tissue. The light may be across a broad spectrum or at a plurality of discrete frequencies or at a single frequency at 1402. For example, the light may be emitted using a broad spectrum light source or multiple LEDs transmitting at discrete wavelengths or a tunable laser transmitting at one or more frequencies. The spectral response of light (e.g. either transmitted through the living tissue or reflected by the living tissue) is detected at 1404. The spectral response is analyzed at a plurality of wavelengths (and ranges of +/−20 to 50 nm around these wavelengths) at 1406. In one aspect, the systolic and diastolic points are determined at the plurality of wavelengths and the L values are calculated using the systolic and diastolic points. In one aspect, the L values are determined at incremental wavelengths, such as at 1 nm or 1.5 nm or 2 nm incremental wavelengths. In another aspect, the L values are calculated for a set of predetermined wavelengths. A ratio R value may also be determined using L values derived from a first spectral response obtained for a first wavelength (and in one aspect including a range of +/−20 to 50 nm) and a spectral response obtained for a second wavelength (and in one aspect including a ranges of +/−20 to 50 nm).

Using the absorption coefficients associated with the plurality of substances and the spectral responses, the concentration levels of a plurality of substances may then be determined at 1408. For example, the intensity of light may be due to absorption by a plurality of substances in the arterial blood flow. For example, $$LN\ (I_{1-n}) = \mu_1 * C_1 + \mu_2 * C_2 + \mu_3 * C_3 \ldots + \mu_n * C_n$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ are known at the wavelengths $\lambda_{1-n}$, then the concentration levels $C_{1-n}$ of multiple substances may be determined.

In another embodiment, the intensity of light at a plurality of wavelengths may be due to absorption by a single substance in the arterial blood flow. For example, a single substance may absorb or reflect a plurality of different wavelengths of light. In this example then, $$LN\ (I_{1-n}) = \mu_1 * C + \mu_2 * C + \mu_3 * C \ldots + \mu_n * C$$

wherein, $I_{1-n}$=intensity of light at wavelengths $\lambda_{1-n}$ $\mu_n$=absorption coefficient of a substance at wavelengths $\lambda_{1-n}$ C=Concentration level of a substance When the absorption coefficients $\mu_{1-n}$ of the single substance are known at the wavelengths $\lambda_{1-n}$, then the concentration level C of the substance may be determined from the spectral response for each of the wavelengths (and in one aspect including a range of 1 nm to 50 nm around each of the wavelengths). Using the spectral response at multiple frequencies provides a more robust determination of the concentration level of the substance.

Figure 15:
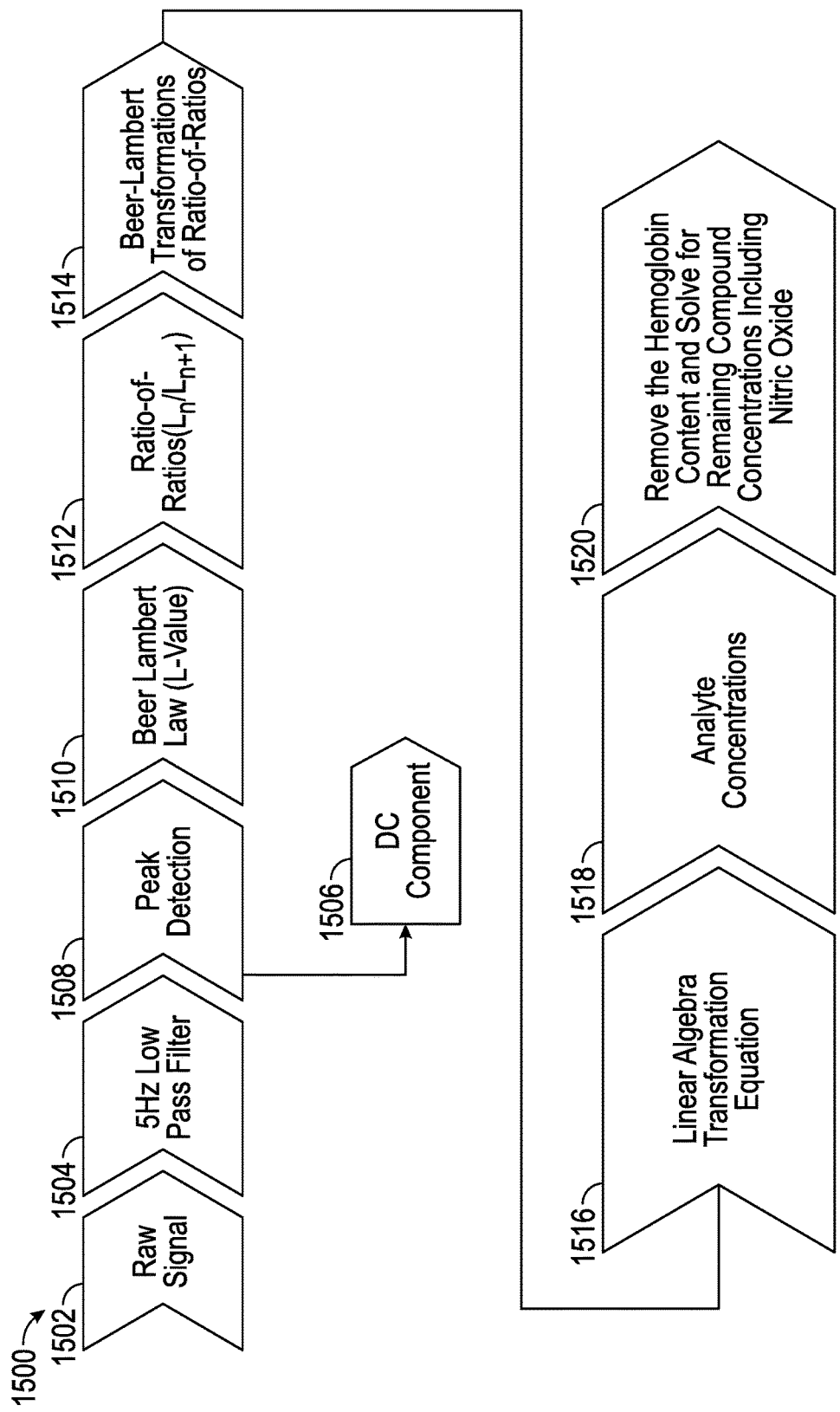
FIG. 15 illustrates a schematic block diagram of an embodiment of a method for determining concentration levels or indicators of substances in pulsating blood flow in more detail.

An example for calculating the concentration of one or more substances over multiple wavelengths may be performed using a linear function, such as is illustrated herein below.

$$LN\ (I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n FIG. 15 illustrates a schematic block diagram of an embodiment of a method 1500 for determining concentration levels or indicators of substances in pulsating blood flow in more detail. The biosensor 100 obtains a spectral response signal at a first wavelength and at a second wavelength at 1502. The spectral response signal includes AC and DC components IAC+DC. A low pass filter is applied to the spectral response signal IAC+DC to isolate the DC component 1506 of the spectral response signal at each wavelength at 1504. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 1508. The systolic and diastolic measurements are compared in order to compute the L values using Beer-Lambert equations at 1510. For example, a logarithmic function may be applied to the ratio of IAC+DC and IDC to obtain an L value for the first wavelength L$\lambda$1 and for the second wavelength L$\lambda$2. The ratio R of the first wavelength L$\lambda$1 and for the second wavelength L$\lambda$2 may then be calculated at 1512. When multiple frequencies are used to determine a concentration level of one or more substances, the the linear function described herein are applied at 1516, and the one or more concentration levels of the substances or analytes are determined at 1518.

In an embodiment, a substances or analyte may be attached in the blood stream to one or more hemoglobin compounds. The concentration level of the hemoglobin compounds may then need to be subtracted from the concentration level of the substance to isolate the concentration level of the substance from the hemoglobin compounds. For example, nitric oxide (NO) is found in the blood stream in a gaseous form and also attached to hemoglobin compounds. Thus, the measurements at $L_{390\ nm}$ to detect nitric oxide may include a concentration level of the hemoglobin compounds as well as nitric oxide.

The hemoglobin compound concentration levels may be determined and subtracted to isolate the concentration level of the substance at 1520. The hemoglobin compounds include, e.g., Oxyhemoglobin [HbO2], Carboxyhemoglobin [HbCO], Methemoglobin [HbMet], and reduced hemoglobin fractions [RHb]. The biosensor 100 may control the PPG circuit 110 to detect the total concentration of the hemoglobin compounds using a center frequency of 660 nm and a range of 1 nm to 50 nm. A method for determining the relative concentration or composition of different kinds of hemoglobin contained in blood is described in more detail in U.S. Pat. No. 6,104,938 issued on Aug. 15, 2000, which is hereby incorporated by reference herein.

Various unexpected results were determined from clinical trials using the biosensor 100. In one aspect, based on the clinical trials, an R value obtained from the ratio $L_{\lambda 1=390\ nm}/$ and $L_{\lambda 2=940}$ was found to be a predictor or indicator of diabetic risk or diabetes as described in more detail herein. In another aspect, based on the clinical trials, the R value obtained from the ratio of $L_{468\ nm}/L_{940\ nm}$, was identified as an indicator of the liver enzyme marker, e.g. P450. In another aspect, based on the clinical trials, the R value obtained from the ratio of $L_{592\ nm}/L_{940\ nm}$, was identified as an indicator of digestion phases, such as phase 1 and phase 2, in the arterial blood flow. In another aspect, the R value from the ratio of $L_{660\ nm}/L_{940\ nm}$, was found to be an indicator of oxygen saturation levels SpO$_2$ in the arterial blood flow. In another aspect, it was determined that the biosensor 100 may determine alcohol levels in the blood using spectral responses for wavelengths at 390 and/or 468 nm. In general, the second wavelength of 940 nm is selected because it has a low absorption coefficient for the targeted substances described herein. Thus, another wavelength other than 940 nm with a low absorption coefficient for the targeted substances (e.g. at least less than 25% of the absorption coefficient of the targeted substance for the first wavelength) may be used instead. For example, the second wavelength of 940 nm may be replaced with 860 nm that has a low absorption coefficient for the targeted substances. In another aspect, the second wavelength of 940 nm may be replaced with other wavelengths, e.g. in the IR range, that have a low absorption coefficient for the targeted substances. In general, it is desired that the spectral response for the first predetermined wavelength have a higher intensity level than the spectral response for the second predetermined wavelength.

In another aspect, it was determined that other proteins or compounds, such as those present or with higher concentrations in the blood with persons having cancer, may be detected using similar PPG techniques described herein with biosensor 100 at one or more other wavelengths. Cancer risk may then be determined using non-invasive testing over a short measurement period of 1-10 minutes. Since the biosensor may operate in multiple frequencies, various health monitoring tests may be performed concurrently. For example, the biosensor 100 may measure for diabetic risk, liver enzymes, alcohol levels, cancer risk or presence of other analytes within a same measurement period using PPG techniques.

Embodiment—Absorption Rate of Medication

The PPG circuit 110 may also detect a concentration level of medication in the epidermal layer of the skin using similar principles under the Beer-Lambert law. For example, a first wavelength is transmitted onto and/or into the epidermal layer that has a high absorption coefficient with respect to the target medication in skin tissue. A second wavelength is also transmitted onto and/or into the epidermal layer of the skin that has a low absorption coefficient with respect to the target medication in skin tissue. The concentration C of the medication may then be determined using Beer-Lambert Law principles. The concentration C is then monitored over a time period to determine the absorption rate. For example, the concentration C may be determined at subsecond intervals during the dosage period and thereafter, e.g. for a predetermined time period thereafter or until the concentration C reaches an undetectable amount. An absorption rate may then be determined based on the administration rate of the medication and the monitored concentration during the dosage period and thereafter.

Embodiment—Adjustments in Response to Positioning of the IDDB System 100

Figure 16:
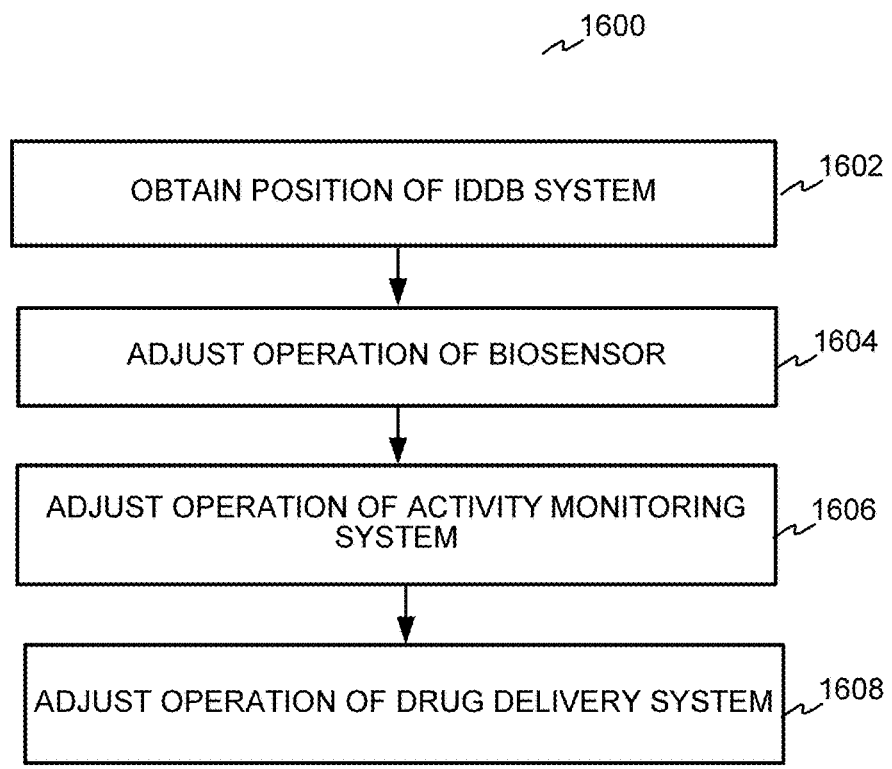
FIG. 16 illustrates a logical flow diagram of an embodiment of a method for adjusting operation of the IDDB system in response to a position of the IDDB system.

FIG. 16 illustrates a logical flow diagram of an embodiment of a method 1600 for adjusting operation of the IDDB system 100 in response to a position of the IDDB system 100. The IDDB system 100 may be positioned on different parts of a patient that exhibit different characteristics. For example, the IDDB system 100 may be positioned on or attached to various areas of the body, e.g. a hand, a wrist, an arm, forehead, chest, abdominal area, ear lobe, fingertip or other area of the skin or body or living tissue. The characteristics of underlying tissue vary depending on the area of the body, e.g. the underlying tissue of an abdominal area has different characteristics than the underlying tissue at a wrist. The operation of the IDDB system 100 may need to be adjusted in response to its positioning due to such varying characteristics of underlying tissue. For example, absorption coefficients may be different for various substances depending on the underlying tissue. As such, different wavelengths or wavelength ranges may be more effective in detecting various substances depending on the underlying tissue.

The IDDB system 100 is configured to obtain position information at 1602. The position information may be input from a user interface. In another aspect, the IDDB system 100 may determine its positioning, e.g. using the activity monitoring circuit 114 and/or PPG circuit 110. For example, the PPG circuit 110 may be configured to detect characteristics of underlying tissue. The IDDB system 100 then correlates the detected characteristics of the underlying tissue with known or predetermined characteristics of underlying tissue (e.g. measured from an abdominal area, wrist, forearm, leg, etc.) to determine its positioning. Information of amount and types of movement from the activity monitor may be used as well.

In response to the determined position and/or detected characteristics of the underlying tissue, the IDDB system 100 is configured to adjust operation of one or more functions or modules. For example, the biosensor 200 may adjust operation of the PPG circuit 110 at 1604. For example, the article, "Optical Properties of Biological Tissues: A Review," by Steven L. Jacques, Phys. Med. Biol. 58 (2013), which is hereby incorporated by reference herein, describes wavelength-dependent behavior of scattering and absorption of different tissues. The PPG circuit 110 may adjust a frequency or wavelength in detection of a concentration level of a substance based on the underlying tissue. The PPG circuit 110 may adjust an absorption coefficient when determining a concentration level of a substance based on Beer-Lambert principles. Other adjustments may also be implemented depending on predetermined or measured characteristics of the underlying tissue.

Adjustments to the activity monitoring circuit 114 may also need to be made depending on positioning as well at 1606. For example, the type and level of movement detected when positioned on a wrist may vary from type and level of movement when positioned on an abdominal area. In another aspect, the biosensor may adjust measurements from the temperature sensor depending on placement, e.g. sensor array measurements may vary from a wrist or forehead.

The drug delivery system 210 may also adjust operation in response to positioning of the IDDB system 100 at 1608. For example, the drug delivery system 210 may automatically adjust administration rate of a medicine depending on positioning due to known or predetermined absorption rates of different tissues.

The IDDB system 100 may also adjust operation in response to the activity level of the patient. For example, the IDDB system 100 may enter rest mode during periods of low activity or periods of sleep.

The IDDB system 100 is thus configured to obtain position information and activity levels and perform adjustments to its operation in response to the position information and activity levels.

Embodiment—EMR Network

Figure 17:
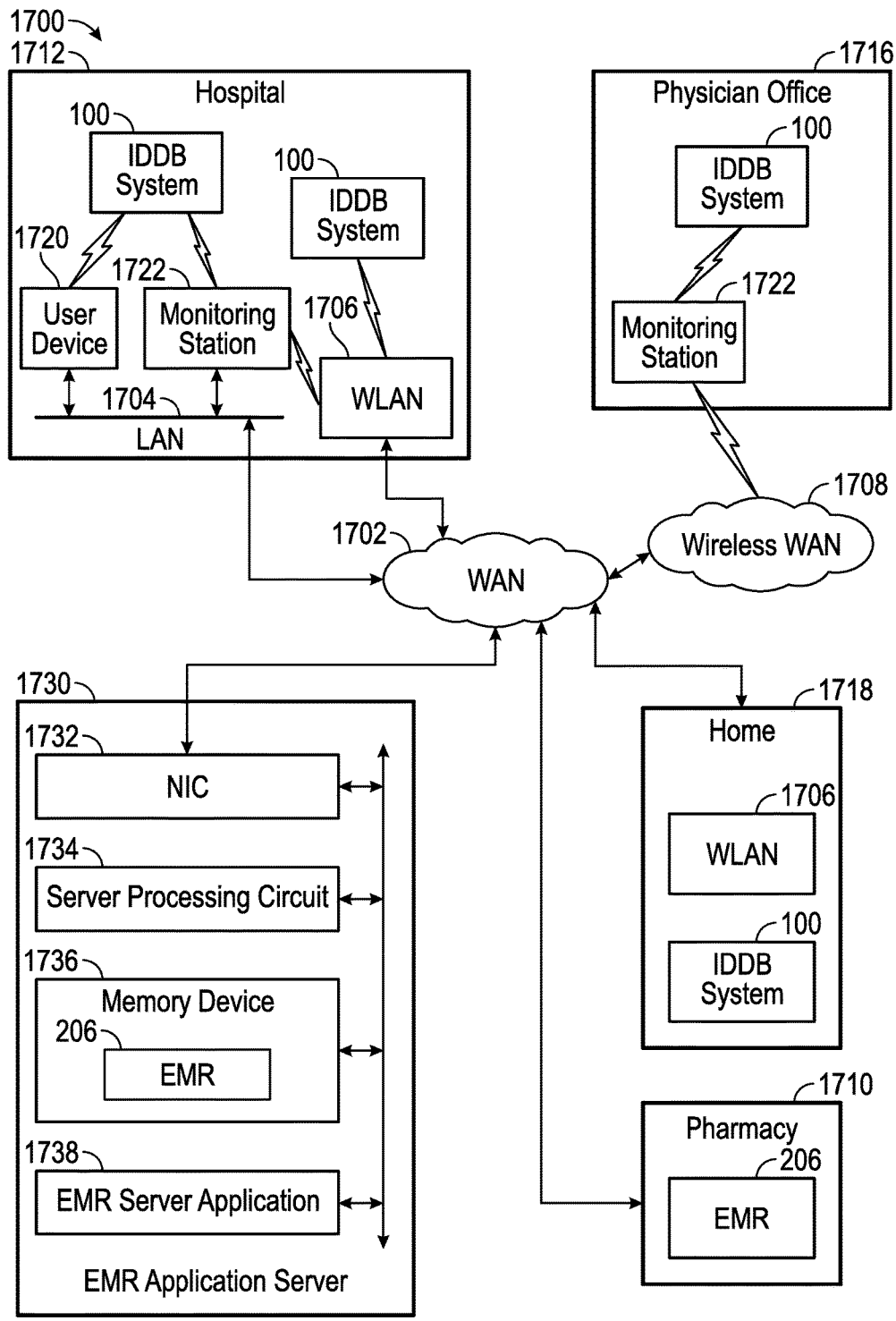
FIG. 17 illustrates a schematic block diagram of an embodiment of an exemplary EMR network in which the IDDB system described herein may operate.

FIG. 17 illustrates a schematic block diagram of an embodiment of an exemplary EMR network 1700 in which the IDDB system 100 described herein may operate. The exemplary EMR network 1700 includes one or more networks that are communicatively coupled, e.g., such as a wide area network (WAN) 1702, a wired local area network (LAN) 1704, a wireless local area network (WLAN) 1706, and/or a wireless wide area network (WAN) 1708. The LAN 1704 and the WLANs 1708 may operate inside a home 1718 or in an enterprise environment, such as a physician's office 1716, pharmacy 1710 or hospital 1712 or other facility. The wireless WAN 1708 may include, for example, a 3G or 4G cellular network, a GSM network, a WIMAX network, an EDGE network, a GERAN network, etc. or a satellite network or a combination thereof. The WAN 1702 includes the Internet, service provider network, other type of WAN, or a combination of one or more thereof.

The IDDB system 100 may communicate to user devices 1720 that may include a smart phone, laptop, desktop, smart tablet, smart watch, or any other electronic device that includes a display for illustrating the patient's vitals. In an embodiment, the user device 1720 may communicate the patient's vitals from the IDDB systems 100 to a monitoring station 1722 or the EMR application server 1730. In another embodiment, the IDDB system 100 may communicate directly with the EMR application server 1730 over the EMR network 1700. For example, an IDDB system 100 may be programmed with a patient identification 208 that is associated with a patient's EMR 206. The IDDB system 100 is then attached to the patient. The IDDB system 100 may then immediately begin to measure a patient's vitals, such as heart rate, pulse, blood oxygen levels, blood glucose or insulin levels, etc. and administer medications. The IDDB system 100 may be used to track progress throughout the patient care chain and provide medical alerts to notify when vitals are critical or reach a certain predetermined threshold. The IDDB system 100 transmits biosensor data and medication dosages, absorption rates, etc. to the EMR network for inclusion in the patient's EMR 206 as well as to a monitoring station 1722, another hospital or physician's office, etc. The IDDB system 100 may be disposable and unique to each patient.

One or more IDDB system 100s are communicatively coupled to an EMR application server 1730 through one or more of the exemplary networks in the EMR network 1700. The EMR application server 1730 includes a network interface circuit 1732 and a server processing circuit 1734. The network interface circuit (NIC) 1732 includes an interface for wireless and/or wired network communications with one or more of the exemplary networks in the EMR network 1700. The network interface circuit 1732 may also include authentication capability that provides authentication prior to allowing access to some or all of the resources of the EMR application server 1730. The network interface circuit 1732 may also include firewall, gateway and proxy server functions.

The EMR application server 1730 also includes a server processing circuit 1734 and a memory device 1736. For example, the memory device 1736 is a non-transitory, processor readable medium that stores instructions which when executed by the server processing circuit 1734, causes the server processing circuit 1734 to perform one or more functions described herein. In an embodiment, the memory device 1736 stores a patient EMR 206 that includes biosensor data transmitted to the EMR application server 1730 from the plurality of IDDB systems 100 and/or user devices 1720.

The EMR application server 1730 includes an EMR server application 1738. The EMR server application 1738 is operable to communicate with the IDDB systems 100, user devices 1720 or monitoring stations 1722. The EMR server application 1738 may be a web-based application supported by the EMR application server 1730. For example, the EMR application server 1730 may be a web server and support the EMR server application 1738 via a website. In another embodiment, the EMR server application 1738 is a stand-alone application that is downloaded to the user devices 1720 by the EMR application server 1730 and is operable on the user devices 1720 without access to the EMR application server 1730 or only needs to accesses the EMR application server 1730 for additional information, such as biosensor data.

The EMR application server 1730 may also be operable to communicate with a pharmacy 1710 or other third party health care provider over the EMR network 1700 to provide biosensor data and receive instructions on dosages of medication. For example, the EMR server application 1738 may transmit heart rate information or pulse rate information or medication absorption rates or blood concentration levels of one or more relevant substances to a physician's office 1716. The EMR server application 1738 may also transmit alerts to a doctor's office, pharmacy or hospital or other caregiver or business over the communication network 1220. The EMR server application 1738 may also receive instructions from a doctor's office, pharmacy or hospital or other caregiver regarding a prescription or administration of a dosage of medication. The EMR server application 1738 may then transmit the instructions to the IDDB system 100. The instructions may include a dosage amount, rate of administration or frequency of dosages of a medication. The IDDB system 100 may then administer the medication automatically as per the transmitted instructions.

Embodiment—Interoperability of the IDDB Systems and Other Devices

Figure 18:
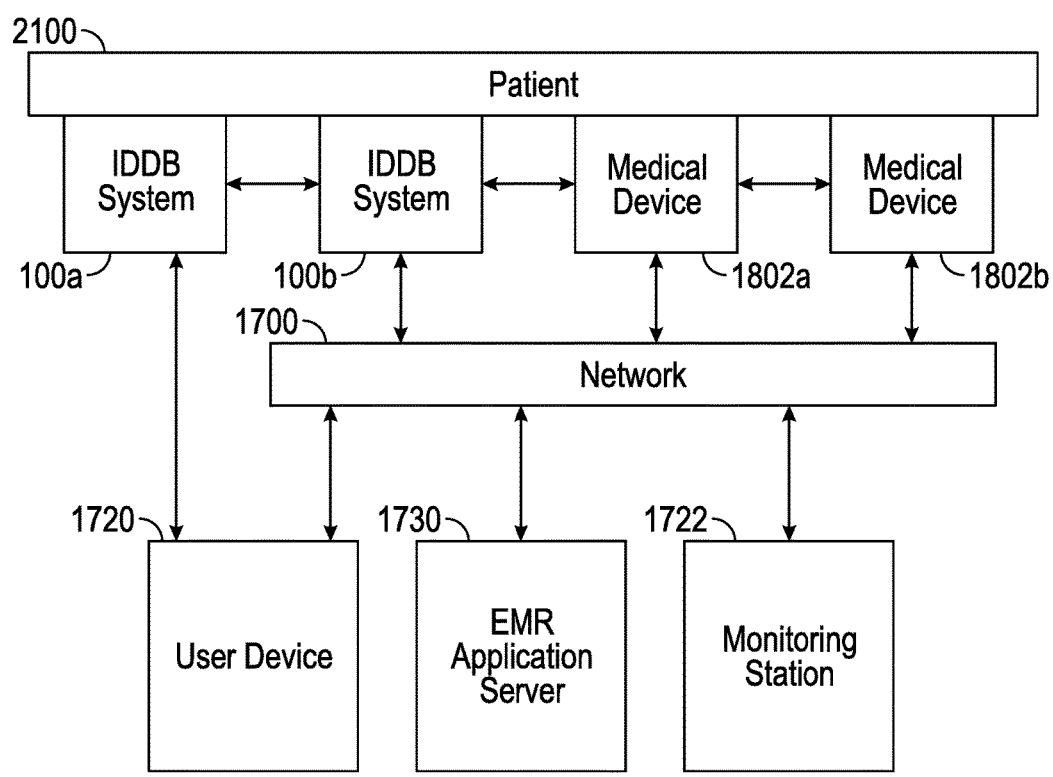
FIG. 18 illustrates a schematic block diagram of an embodiment of a network illustrating interoperability of a plurality of IDDB systems.

FIG. 18 illustrates a schematic block diagram of an embodiment of a network illustrating interoperability of a plurality of IDDB systems 100. An IDDB system 100 interfacing with a patient may communicate with one or more other IDDB systems 100 interfacing with the patient directly or indirectly through a WLAN or other type of network as illustrated in the EMR Network 1700 of FIG. 17. For example, IDDB system 100a may include a needle sensing system 608 or PPG circuit 110 configured to detect a glucose and/or insulin indicators/concentration levels. For better detection, IDDB system 100a is positioned on a wrist. IDDB system 100b may include a drug delivery system 210 configured to administer insulin to the patient and is positioned on an abdominal area of the patient. In use, IDDB system 100a continuously monitors glucose and/or insulin concentration levels/indicators and then communicates either directly or indirectly the detected concentration levels/indicators to IDDB system 100b. IDDB system 100b then administers a dosage of insulin at an administration rate and/or frequency rate in response to the detected concentration levels/indicators.

In another embodiment, one or more IDDB systems 100 may communicate directly or indirectly with one or more other types of medical devices interfacing with a same patient, such as first medical device 1802a and a second medical device 1802b. For example, the first medical device 1802a may include an insulin pump, e.g. on body insulin pump or catheter tethered drip system. In use, IDDB system 100a monitors glucose and/or insulin indicators or concentration levels in the patient using a PPG circuit 110 and/or needle sensing system 608. In response to the detected glucose and/or insulin concentration/indicators, IDDB system 100a communicates either directly or indirectly administration instructions to the first medical device 1802a. The administration instructions may include dosage amount, administration rate and/or frequency rate. In response to the administration instructions, the first medical device 1802a administers an insulin infusion to the patient. The IDDB system 100 may continuously monitor glucose/insulin indicators or concentration levels and provide automatic instructions to the the first medical device 1802a on administration of insulin.

In another example, a plurality of IDDB systems 100, such as the first IDDB system 100a and the second IDDB system 100b, may be positioned on a patient to monitor an ECG of the patient. The plurality of IDDB systems 100 may communicate the ECG measurements directly or indirectly to each other to generate an electrocardiogram. The electrocardiogram is transmitted to an EMR application server 1730 or monitoring station 1722 or to a user device 1720. The EMR application server 1730 or monitoring station 1722 or user device 1720 may then generate and/or display the electrocardiogram from the ECG measurements. Based on the electrocardiogram, a doctor or user may provide instruction to the second medical device 1802b. For example, the second medical device 1802b may include a pacemaker or drug delivery system 210.

In another example, the first IDDB system 100a may include a PPG circuit 110 configured to detect alcohol levels in arterial blood flow. The user device may include a locking system installed in an ignition system of a vehicle. In order to start the vehicle, the first IDDB system 100a detects the blood alcohol concentration (BAC) of the patient. Then, the first IDDB system 100a determines whether the blood alcohol concentration (BAC) is above or below a preset legal limit. If it is below this limit, the IDDB system 100 communicates an instruction to the user device 1720 to unlock the ignition to allow starting of the vehicle. If it is above the limit, the IDDB system 100 instructs the user device 1720 to lock the ignition to prevent starting of the vehicle. The IDDB system 100 may be more accurate and convenient than current breathe analyzers.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. §112(f) as a "means-plus-function" type element, unless the element is expressly recited using the phrase "means for" or, in the case of a method claim, the element is recited using the phrase "step for."

The invention claimed is:

1. An integrated drug delivery and biosensor (IDDB) system, comprising:
   a patch configured for attaching to a patient;
   a drug delivery system coupled to the patch, wherein the drug delivery system is configured to administer a dosage of medication at an administration rate at an upper epidermal layer of skin to the patient;
   a biosensor system coupled to the patch, wherein the biosensor system is configured to:
      monitor biosensor data of the patient, wherein the biosensor data includes one or more of: respiratory rate, heart rate or blood pressure;
      continuously monitor an absorption rate of the medication into the upper epidermal layer of skin and surrounding tissue and in arterial blood flow of the patient; and
      continuously monitor a concentration of a substance in the arterial blood flow, wherein the concentration of the substance corresponds to a concentration of the medication;
   wherein the drug delivery system is configured to alter the dosage of the medication and the administration rate of the medication in response to: the biosensor data; the absorption rate of the medication into the upper epidermal layer of skin and surrounding tissue and in the arterial blood flow; and the concentration of the substance in the arterial blood flow.

2. The IDDB system of claim 1, wherein the drug delivery system includes one or more needles and is configured to administer the dosage of the medication at the administration rate through the one or more needles into the upper epidermal layer of the skin.

3. The IDDB system of claim 2, wherein the biosensor includes at least a PPG circuit, wherein the PPG circuit includes:
   a light source configured to emit light directed at skin of the patient at a plurality of frequencies;
   a photodetector circuit configured to detect spectral responses of reflected light from the skin and surrounding tissue at the plurality of frequencies; and
   a processing circuit configured to:
      process the spectral response at a plurality of frequencies; and
      obtain an absorption rate of the medication into the surrounding tissue and the arterial blood flow using the spectral response.

4. The IDDB system of claim 3, wherein the drug delivery system is configured to alter at least one of the dosage of the medication or the administration rate of the medication or frequency of dosage of the medication in response to the absorption rate of the medication into the surrounding tissue and the arterial blood flow.

5. The IDDB system of claim 1, wherein the biosensor system is further configured to:
   determine one or more of: respiratory rate, heart rate or blood pressure has exceeded a predetermined threshold indicating an allergic reaction; and
   transmit instructions to the drug delivery system to halt the administration of the dosage of the medication.

6. The IDDB system of claim 1, wherein the biosensor includes at least a photoplethysmograpy (PPG) circuit, wherein the PPG circuit includes:
   a light source configured to emit light directed at skin of the patient at a plurality of frequencies;
   a photodetector circuit configured to detect spectral responses of reflected light from the skin and surrounding tissue at the plurality of frequencies; and
   a PPG circuit configured to:
      emit light having at least a first wavelength responsive to the substance directed at an outer epidermal layer of skin tissue of a patient;
      emit light having at least a second wavelength with a low absorption coefficient for the substance directed at the outer epidermal layer of skin tissue of the patient;
      generate a first spectral response for light around the first wavelength responsive to substance levels reflected from the outer epidermal layer of the skin tissue of the patient;
      generate a second spectral response for light around the second wavelength with a low absorption coefficient for substance reflected from the outer epidermal layer of the skin tissue of the patient;
   a processing circuit configured to obtain an indicator of a concentration level of substance of the patient by:
      isolating a systolic point and a diastolic point in the first spectral response and obtain a value $L_{\lambda 1}$ using a ratio of the systolic point and the diastolic point in the first spectral response;
      isolating a systolic point and a diastolic point in the second spectral response and obtain a value $L_{\lambda 2}$ using a ratio of the systolic point and diastolic point in the second spectral response;
      obtaining a value $R_{\lambda 1, \lambda 2}$ from a ratio of the value $L_{\lambda 1}$ and the value $L_{\lambda 2}$, wherein the value $R_{\lambda 1, \lambda 2}$ is the indicator of the concentration level of substance of the patient;
      obtaining a arterial blood medication concentration level in the arterial blood flow of the patient from a calibration table using the value $R_{\lambda 1, \lambda 2}$, wherein the calibration table includes a range of $R_{\lambda 1, \lambda 2}$ values with substance and correlated medicine concentration levels; and
   a processing circuit configured to:
      process the spectral responses at the plurality of frequencies; and
      configure the system to calculate and process the absorption amount of only the upper epidermal layer of skin of at least one substance and/or obtain a concentration level of at least one substance in arterial blood flow of the patient.

7. The IDDB system of claim 6, wherein the processing circuit is configured to process the spectral responses at the plurality of wavelengths by:
  isolating a systolic point and a diastolic point in a first spectral response and obtain a value $L_{\lambda 1}$ using a ratio of the systolic point and the diastolic point in the first spectral response;
  isolating a systolic point and a diastolic point in a second spectral response and obtain a value $L_{\lambda 2}$ using a ratio of the systolic point and diastolic point in the second spectral response; and
  obtaining a value $R_{\lambda 1, \lambda 2}$ from a ratio of the value $L_{\lambda 1}$ and the value $L_{\lambda 2}$.

8. The IDDB system of claim 1, wherein the IDDB system is further configured to:
  obtain position information of the biosensor and activity level; and
  adjust operation of the biosensor system and the drug delivery system in response to the position information of the biosensor and the activity level.

9. The IDDB system 100 of claim 1, further comprising:
  a wireless transceiver coupled to the patch for transmitting biosensor data and the dosage and the administration rate of the medication to one or more devices in an EMR network.

10. An method operable by an integrated drug delivery and biosensor (IDDB), comprising:
  administering a dosage of medication at an administration rate from a drug delivery system integrated onto the patch for attaching to a patient;
  monitoring biosensor data of the patient using a biosensor integrated onto the patch, wherein the biosensor data includes one or more of: respiratory rate, heart rate or blood pressure;
  monitoring absorption rate using the integrated biosensor of the medication into surrounding tissue and arterial blood flow;
  monitoring concentration by the integrated biosensor of a substance in arterial blood flow, wherein the concentration of the substance corresponds to a concentration of the medication; and
  altering the dosage of the medication and the administration of the medication by the drug delivery system in response to the biosensor data, the absorption rate of the medication into the surrounding tissue and into the arterial blood flow, and the concentration of the substance in the arterial blood flow.

11. The method of claim 10, further comprising:
  administering the dosage of the medication at the administration rate through one or more needles protruding from the patch into at least an upper epidermal layer of the skin.

12. The method of claim 10, further comprising:
  determining one or more of: respiratory rate, heart rate or blood pressure has exceeded a predetermined threshold indicating an allergic reaction; and
  transmitting instructions to the drug delivery system to halt the administration of the dosage of the medication.

13. The method of claim 10, further comprising:
  emitting light directed at skin of the patient at a plurality of frequencies by a photoplethysmograpy (PPG) circuit of the biosensor;
  detecting spectral responses of reflected light from the skin and surrounding tissue at the plurality of frequencies by a photodetector circuit of the biosensor;
  processing the spectral responses at the plurality of frequencies; and
  obtaining a concentration level of at least one substance in arterial blood flow of the patient.

14. The method of claim 10, further comprising:
  processing the spectral responses at the plurality of wavelengths by:
    isolating a systolic point and a diastolic point in a first spectral response and obtain a value $L_{\lambda 1}$ using a ratio of the systolic point and the diastolic point in the first spectral response;
    isolating a systolic point and a diastolic point in a second spectral response and obtain a value $L_{\lambda 2}$ using a ratio of the systolic point and diastolic point in the second spectral response; and
    obtaining a value $R_{\lambda 1, \lambda 2}$ from a ratio of the value $L_{\lambda 1}$ and the value $L_{\lambda 2}$.

15. The method of claim 10, further comprising:
  emitting light directed at skin of the patient at a plurality of frequencies by a light source in the biosensor;
  detecting spectral responses of reflected light from the skin and surrounding tissue at the plurality of frequencies by a photodetector circuit in the biosensor;
  processing the spectral response at a plurality of frequencies; and
  obtaining an absorption rate of the medication using the spectral response.

16. The method of claim 15, further comprising:
  altering at least one of the dosage of the medication or the administration rate of the medication or frequency of dosage of the medication in response to the absorption rate of the medication.

17. The method of claim 10, further comprising:
  obtaining at least one of: position information and activity level; and
  adjusting operation of at least one of the biosensor system or the drug delivery system in response to at least one of the position information or the activity level.

18. The method of claim 10, further comprising:
  transmitting biosensor data and the dosage and the administration rate of the medication to one or more devices in an EMR network.

19. An integrated drug delivery and biosensor (IDDB) system, comprising:
  a patch configured for attaching to a patient;
  a drug delivery system coupled to the patch, wherein the drug delivery system is configured to administer a dosage of insulin at an administration rate to the patient;
  a biosensor system coupled to the patch configured to continuously monitor a blood glucose concentration level in the arterial blood flow of the patient, wherein the biosensor system includes:
    a PPG circuit configured to:
      emit light having at least a first wavelength responsive to nitric oxide (NO) levels directed at an outer epidermal layer of skin tissue of a patient;
      emit light having at least a second wavelength with a low absorption coefficient for nitric oxide (NO) directed at the outer epidermal layer of skin tissue of the patient;
      generate a first spectral response for light around the first wavelength responsive to NO levels reflected from the outer epidermal layer of the skin tissue of the patient;
      generate a second spectral response for light around the second wavelength with a low absorption coefficient for NO reflected from the outer epidermal layer of the skin tissue of the patient;

a processing circuit configured to obtain an indicator of a concentration level of NO of the patient by:
  isolating a systolic point and a diastolic point in the first spectral response and obtain a value $L_{\lambda 1}$ using a ratio of the systolic point and the diastolic point in the first spectral response;
  isolating a systolic point and a diastolic point in the second spectral response and obtain a value $L_{\lambda 2}$ using a ratio of the systolic point and diastolic point in the second spectral response;
  obtaining a value $R_{\lambda 1, \lambda 2}$ from a ratio of the value $L_{\lambda 1}$ and the value $L_{\lambda 2}$, wherein the value $R_{\lambda 1, \lambda 2}$ is the indicator of the concentration level of NO of the patient;
  obtaining a blood glucose concentration level in the arterial blood flow of the patient from a calibration table using the value $R_{\lambda 1, \lambda 2}$, wherein the calibration table includes a range of $R_{\lambda 1, \lambda 2}$ values and correlated blood glucose concentration levels; and
wherein the IDDB system is configured to alter the dosage of the insulin and the administration rate of the insulin in response to the blood glucose concentration level in the arterial blood flow.

20. The IDDB system of claim 19, wherein the drug delivery system includes one or more needles and is configured to administer the dosage of the insulin at the administration rate through the one or more needles into an upper epidermal layer of the skin.

21. The IDDB system of claim 20, wherein the PPG circuit is further configured to:
  measure an absorption rate of the insulin into the upper epidermal layer of the skin and surrounding tissue; and
  wherein the IDDB system is further configured to alter the administration rate of the insulin in response to the absorption rate of the insulin into the upper epidermal layer of the skin and the surrounding tissue.

22. The IDDB system of claim 21, wherein the PPG circuit is further configured to:
  monitor biosensor data of the patient, wherein the biosensor data includes one or more of: respiratory rate, heart rate or blood pressure; and
  wherein the IDDB system is further configured to alter the administration rate of the insulin in response to the biosensor data of the patient.

23. The IDDB system of claim 22, wherein the drug delivery system further comprises:
  a drug receptacle coupled to the one or more needles; and
  a hydrogen fuel cell configured to pressurize the drug receptacle and force the dosage of the insulin at the administration rate through the one or more needles into the upper epidermal layer of the skin of the patient.

* * * * *